United States Patent
Romesburg

(10) Patent No.: US 11,375,902 B2
(45) Date of Patent: Jul. 5, 2022

(54) SYSTEMS AND METHODS FOR VARIABLE FILTER ADJUSTMENT BY HEART RATE METRIC FEEDBACK

(71) Applicant: Valencell, Inc., Raleigh, NC (US)

(72) Inventor: Eric Douglas Romesburg, Chapel Hill, NC (US)

(73) Assignee: Valencell, Inc., Raleigh, NC (US)

( * ) Notice: Subject to any disclaimer, the term of this patent is extended or adjusted under 35 U.S.C. 154(b) by 316 days.

(21) Appl. No.: 16/683,884

(22) Filed: Nov. 14, 2019

(65) Prior Publication Data

US 2020/0077899 A1    Mar. 12, 2020

Related U.S. Application Data

(63) Continuation of application No. 15/784,960, filed on Oct. 16, 2017, now Pat. No. 10,512,403, which is a
(Continued)

(51) Int. Cl.
*A61B 5/00* (2006.01)
*A61B 5/024* (2006.01)
(Continued)

(52) U.S. Cl.
CPC .......... *A61B 5/0095* (2013.01); *A61B 5/0059* (2013.01); *A61B 5/0245* (2013.01);
(Continued)

(58) Field of Classification Search
CPC .......................... A61B 5/0059; A61B 5/02416
See application file for complete search history.

(56) References Cited

U.S. PATENT DOCUMENTS

| 3,595,219 A | 7/1971 | Friedlander et al. |
| 4,240,882 A | 12/1980 | Ang et al. |

(Continued)

FOREIGN PATENT DOCUMENTS

| AU | 2015101130 | 10/2015 |
| CN | 101212927 | 7/2008 |

(Continued)

OTHER PUBLICATIONS

Asada et al. "Mobile Monitoring with Wearable Photoplethysmographic Biosensors" IEEE Engineering in Medicine and Biology Magazine (pp. 28-40) (May/Jun. 2003).
(Continued)

*Primary Examiner* — Rex R Holmes
*Assistant Examiner* — Jennifer L Ghand
(74) *Attorney, Agent, or Firm* — Myers Bigel, P.A.

(57) ABSTRACT

A physiological signal processing system for a physiological waveform that includes a cardiovascular signal component provides a variable high pass filter that is responsive to the physiological waveform, and that is configured to high pass filter the physiological waveform in response to a corner frequency that is applied. A heart rate metric extractor is responsive to the variable high pass filter and is configured to extract a heart rate metric from the physiological waveform that is high pass filtered. A corner frequency adjuster is responsive to the heart rate metric extractor and is configured to determine the corner frequency that is applied to the variable high pass filter, based on the heart rate metric that was extracted. Analogous methods may also be provided.

22 Claims, 12 Drawing Sheets

Related U.S. Application Data continuation of application No. 14/124,465, filed as application No. PCT/US2012/048079 on Jul. 25, 2012, now Pat. No. 9,801,552.

(60) Provisional application No. 61/514,099, filed on Aug. 2, 2011.

(51) Int. Cl.
| | |
|---|---|
| *A61B 5/0245* | (2006.01) |
| *A61B 5/316* | (2021.01) |
| *A61B 5/318* | (2021.01) |
| *A61B 5/369* | (2021.01) |
| *A61B 5/08* | (2006.01) |
| *A61B 5/0205* | (2006.01) |

(52) U.S. Cl.
CPC .......... *A61B 5/02416* (2013.01); *A61B 5/316* (2021.01); *A61B 5/318* (2021.01); *A61B 5/369* (2021.01); *A61B 5/725* (2013.01); *A61B 5/7225* (2013.01); *A61B 5/7278* (2013.01); *A61B 5/0205* (2013.01); *A61B 5/0816* (2013.01)

(56) References Cited

U.S. PATENT DOCUMENTS

| | | |
|---|---|---|
| 4,281,645 A | 8/1981 | Jobsis |
| 4,331,154 A | 5/1982 | Broadwater et al. |
| 4,371,406 A | 2/1983 | Li |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,586,513 A | 5/1986 | Hamaguri |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,952,890 A | 8/1990 | Swanson |
| 4,952,928 A | 8/1990 | Carroll et al. |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,139,025 A | 8/1992 | Lewis et al. |
| 5,143,078 A | 9/1992 | Mather et al. |
| 5,226,417 A | 7/1993 | Swedlow et al. |
| 5,237,994 A | 8/1993 | Goldberger |
| 5,299,570 A | 4/1994 | Hatschek |
| 5,348,002 A | 9/1994 | Caro |
| 5,357,969 A * | 10/1994 | Herleikson .......... A61N 1/3925 600/508 |
| 5,377,100 A | 12/1994 | Pope et al. |
| 5,386,819 A | 2/1995 | Kaneko et al. |
| 5,431,170 A | 7/1995 | Mathews |
| 5,448,082 A | 9/1995 | Kim |
| 5,482,036 A | 1/1996 | Diab et al. |
| 5,492,129 A | 2/1996 | Greenberger |
| 5,494,043 A | 2/1996 | O'Sullivan et al. |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,817,008 A | 10/1998 | Rafert et al. |
| 5,820,560 A | 10/1998 | Sinderby et al. |
| 5,846,190 A | 12/1998 | Woehrle |
| 5,853,005 A | 12/1998 | Scanlon |
| 5,904,654 A | 5/1999 | Wohltmann et al. |
| 5,938,593 A | 8/1999 | Ouellette |
| 5,954,644 A | 9/1999 | Dettling et al. |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,006,119 A | 12/1999 | Soller et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,122,042 A | 9/2000 | Wunderman et al. |
| 6,148,229 A | 11/2000 | Morris, Sr. et al. |
| 6,155,983 A | 12/2000 | Kosuda et al. |
| 6,161,042 A * | 12/2000 | Hartley .............. A61N 1/36521 607/20 |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,267,721 B1 | 7/2001 | Welles |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |

(56) References Cited

U.S. PATENT DOCUMENTS

| | | |
|---|---|---|
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Romhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,048,687 B1 | 5/2006 | Reuss et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,144,375 B2 | 12/2006 | Kosuda |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo |
| 7,341,559 B2 | 3/2008 | Schulz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar, Jr. et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | Leboeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | Leboeuf et al. |
| 8,233,955 B2 | 7/2012 | Al-Ali et al. |
| 8,251,903 B2 | 8/2012 | Leboeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | Leboeuf et al. |
| 8,323,982 B2 | 12/2012 | Leboeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | Leboeuf et al. |
| 8,647,270 B2 | 2/2014 | Leboeuf et al. |
| 8,652,040 B2 | 2/2014 | Leboeuf et al. |
| 8,652,409 B2 | 2/2014 | Leboeuf et al. |
| 8,679,008 B2 | 3/2014 | Hughes et al. |
| 8,700,111 B2 | 4/2014 | Leboeuf et al. |
| 8,702,607 B2 | 4/2014 | Leboeuf et al. |
| 8,730,048 B2 | 5/2014 | Shen et al. |
| 8,788,002 B2 | 7/2014 | Leboeuf et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,996,332 B2 | 3/2015 | Kahn |
| 9,005,129 B2 | 4/2015 | Venkatraman et al. |
| 9,044,180 B2 | 6/2015 | Leboeuf et al. |
| 9,289,175 B2 | 3/2016 | Leboeuf et al. |
| 9,687,162 B2 | 6/2017 | Vetter et al. |
| 9,808,204 B2 | 11/2017 | Leboeuf et al. |
| 9,943,266 B2 | 4/2018 | Adams et al. |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0173780 A1 | 11/2002 | Altshuler et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0065269 A1 | 4/2003 | Vetter et al. |
| 2003/0083583 A1* | 5/2003 | Kovtun .................. A61B 5/725 |
| | | 600/509 |
| 2003/0109030 A1 | 6/2003 | Uchida et al. |
| 2003/0109791 A1 | 6/2003 | Kondo et al. |
| 2003/0130586 A1 | 7/2003 | Starobin et al. |
| 2003/0181795 A1 | 9/2003 | Suzuki et al. |
| 2003/0181798 A1 | 9/2003 | Al-Ali |
| 2003/0181817 A1 | 9/2003 | Mori |
| 2003/0187341 A1* | 10/2003 | Sackner ................ A61B 5/725 |
| | | 600/388 |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2003/0233051 A1 | 12/2003 | Verjus et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0039254 A1 | 2/2004 | Stivoric et al. |
| 2004/0054291 A1 | 3/2004 | Schulz et al. |
| 2004/0073455 A1 | 4/2004 | McConnochie et al. |
| 2004/0075677 A1 | 4/2004 | Loyall et al. |
| 2004/0077934 A1 | 4/2004 | Massad |
| 2004/0081621 A1 | 4/2004 | Arndt et al. |
| 2004/0082842 A1 | 4/2004 | Lumba et al. |
| 2004/0097796 A1 | 5/2004 | Berman et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0158167 A1 | 8/2004 | Smith et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |

(56) References Cited

U.S. PATENT DOCUMENTS

| | | |
|---|---|---|
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0036212 A1 | 2/2005 | Saito |
| 2005/0038349 A1 | 2/2005 | Choi et al. |
| 2005/0043600 A1 | 2/2005 | Diab et al. |
| 2005/0043630 A1 | 2/2005 | Buchert |
| 2005/0058456 A1 | 3/2005 | Yoo |
| 2005/0059870 A1 | 3/2005 | Aceti |
| 2005/0070809 A1 | 3/2005 | Acres |
| 2005/0084666 A1 | 4/2005 | Pong et al. |
| 2005/0100866 A1 | 5/2005 | Arnone et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller, III et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0240087 A1 | 10/2005 | Keenan et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0074333 A1 | 4/2006 | Huiku |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0287590 A1 | 12/2006 | McEowen |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altshuler et al. |
| 2007/0063850 A1 | 3/2007 | Devaul et al. |
| 2007/0073124 A1 | 3/2007 | Li et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1* | 4/2007 | Stahmann ............ A61B 5/0205 600/485 |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0118054 A1 | 5/2007 | Pinhas et al. |
| 2007/0123763 A1 | 5/2007 | Al-Ali et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0146890 A1 | 6/2008 | Leboeuf et al. |
| 2008/0146892 A1 | 6/2008 | Leboeuf et al. |
| 2008/0154098 A1 | 6/2008 | Morris et al. |
| 2008/0154105 A1 | 6/2008 | LeMay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221414 A1 | 9/2008 | Baker, Jr. |
| 2008/0221461 A1 | 9/2008 | Zhou et al. |
| 2008/0249594 A1 | 10/2008 | Dietrich et al. |
| 2008/0287752 A1 | 11/2008 | Stroetz et al. |
| 2008/0312517 A1 | 12/2008 | Genoe et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0010556 A1 | 1/2009 | Uchibayashi et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |

(56) References Cited

U.S. PATENT DOCUMENTS

| | | |
|---|---|---|
| 2009/0112071 A1 | 4/2009 | Leboeuf et al. |
| 2009/0112101 A1 | 4/2009 | Furness, III et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0281435 A1 | 11/2009 | Ahmed et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney, III et al. |
| 2010/0185105 A1 | 7/2010 | Baldinger |
| 2010/0217100 A1 | 8/2010 | Leboeuf et al. |
| 2010/0217102 A1 | 8/2010 | Leboeuf et al. |
| 2010/0217103 A1 | 8/2010 | Abdul-Hafiz et al. |
| 2010/0222655 A1* | 9/2010 | Starr .............. A61B 5/0082 600/310 |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0066007 A1 | 3/2011 | Banet et al. |
| 2011/0081037 A1 | 4/2011 | Oh et al. |
| 2011/0098112 A1 | 4/2011 | Leboeuf et al. |
| 2011/0105869 A1 | 5/2011 | Wilson et al. |
| 2011/0112382 A1 | 5/2011 | Li et al. |
| 2011/0130638 A1 | 6/2011 | Raridan |
| 2011/0142371 A1 | 6/2011 | King et al. |
| 2011/0178564 A1 | 7/2011 | Keefe |
| 2011/0288379 A1 | 11/2011 | Wu |
| 2012/0030547 A1 | 2/2012 | Raptis et al. |
| 2012/0095303 A1 | 4/2012 | He |
| 2012/0150052 A1 | 6/2012 | Buchheim et al. |
| 2012/0156933 A1 | 6/2012 | Kreger et al. |
| 2012/0172702 A1 | 7/2012 | Koyrakh et al. |
| 2012/0179011 A1 | 7/2012 | Moon et al. |
| 2012/0190948 A1 | 7/2012 | Vetter et al. |
| 2012/0197093 A1 | 8/2012 | Leboeuf et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0277548 A1 | 11/2012 | Burton |
| 2012/0296184 A1 | 11/2012 | Leboeuf et al. |
| 2013/0053661 A1 | 2/2013 | Alberth et al. |
| 2013/0072765 A1 | 3/2013 | Kahn et al. |
| 2013/0131519 A1 | 5/2013 | Leboeuf et al. |
| 2013/0197377 A1 | 8/2013 | Kishi et al. |
| 2013/0245387 A1 | 9/2013 | Patel |
| 2013/0336495 A1 | 12/2013 | Burgett et al. |
| 2014/0012105 A1 | 1/2014 | Leboeuf et al. |
| 2014/0051940 A1 | 2/2014 | Messerschmidt |
| 2014/0051948 A1 | 2/2014 | Leboeuf et al. |
| 2014/0052567 A1 | 2/2014 | Bhardwaj et al. |
| 2014/0058220 A1 | 2/2014 | Leboeuf et al. |
| 2014/0073486 A1 | 3/2014 | Ahmed et al. |
| 2014/0088433 A1 | 3/2014 | Shan |
| 2014/0094663 A1 | 4/2014 | Leboeuf et al. |
| 2014/0100432 A1 | 4/2014 | Golda et al. |
| 2014/0127996 A1 | 5/2014 | Park et al. |
| 2014/0128690 A1 | 5/2014 | Leboeuf |
| 2014/0135596 A1 | 5/2014 | Leboeuf et al. |
| 2014/0140567 A1 | 5/2014 | Leboeuf et al. |
| 2014/0171755 A1 | 6/2014 | Leboeuf et al. |
| 2014/0213863 A1 | 7/2014 | Loseu et al. |
| 2014/0219467 A1 | 8/2014 | Kurtz |
| 2014/0228649 A1 | 8/2014 | Rayner et al. |
| 2014/0235967 A1 | 8/2014 | Leboeuf et al. |
| 2014/0235968 A1 | 8/2014 | Leboeuf et al. |
| 2014/0236531 A1 | 8/2014 | Carter |
| 2014/0243617 A1 | 8/2014 | Leboeuf et al. |
| 2014/0243620 A1 | 8/2014 | Leboeuf et al. |
| 2014/0249381 A1 | 9/2014 | Leboeuf et al. |
| 2014/0275852 A1 | 9/2014 | Hong et al. |
| 2014/0275854 A1 | 9/2014 | Venkatraman et al. |
| 2014/0275855 A1 | 9/2014 | Leboeuf et al. |
| 2014/0276119 A1 | 9/2014 | Venkatraman et al. |
| 2014/0287833 A1 | 9/2014 | Leboeuf et al. |
| 2014/0288392 A1 | 9/2014 | Hong et al. |
| 2014/0288396 A1 | 9/2014 | Leboeuf et al. |
| 2014/0288436 A1 | 9/2014 | Venkatraman et al. |
| 2014/0323829 A1 | 10/2014 | Leboeuf et al. |
| 2014/0323830 A1 | 10/2014 | Leboeuf et al. |
| 2014/0323880 A1 | 10/2014 | Ahmed et al. |
| 2014/0327515 A1 | 11/2014 | Luna et al. |
| 2014/0378844 A1 | 12/2014 | Fei |
| 2015/0011898 A1 | 1/2015 | Romesburg |
| 2015/0018636 A1 | 1/2015 | Romesburg |
| 2015/0025393 A1 | 1/2015 | Hong et al. |
| 2015/0031967 A1 | 1/2015 | Leboeuf et al. |
| 2015/0032009 A1 | 1/2015 | Leboeuf et al. |
| 2015/0057967 A1 | 2/2015 | Albinali |
| 2015/0080741 A1 | 3/2015 | Leboeuf et al. |
| 2015/0080746 A1 | 3/2015 | Bleich et al. |
| 2015/0157269 A1 | 6/2015 | Lisogurski et al. |
| 2015/0190085 A1 | 7/2015 | Nathan et al. |
| 2015/0196256 A1 | 7/2015 | Venkatraman et al. |
| 2015/0250396 A1 | 9/2015 | Ahmed et al. |
| 2015/0265217 A1 | 9/2015 | Penders et al. |
| 2015/0282768 A1 | 10/2015 | Luna et al. |
| 2015/0289820 A1 | 10/2015 | Miller et al. |
| 2015/0305682 A1 | 10/2015 | Leboeuf et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | Leboeuf et al. |
| 2016/0038045 A1 | 2/2016 | Shapiro |
| 2016/0051157 A1 | 2/2016 | Waydo |
| 2016/0089033 A1 | 3/2016 | Saponas et al. |
| 2016/0089086 A1 | 3/2016 | Lin et al. |
| 2016/0094899 A1 | 3/2016 | Aumer et al. |
| 2016/0120476 A1 | 5/2016 | Liu et al. |
| 2016/0206247 A1 | 7/2016 | Morland et al. |
| 2016/0287108 A1 | 10/2016 | Wei et al. |
| 2016/0361021 A1 | 12/2016 | Salehizadeh et al. |
| 2017/0007166 A1 | 1/2017 | Roovers et al. |
| 2017/0034615 A1 | 2/2017 | Mankodi et al. |
| 2017/0112447 A1 | 4/2017 | Aumer et al. |
| 2017/0232294 A1 | 8/2017 | Kruger et al. |
| 2017/0290549 A1 | 10/2017 | Romesburg |
| 2018/0008200 A1 | 1/2018 | Romesburg |
| 2018/0020979 A1 | 1/2018 | Wagner et al. |
| 2018/0146926 A1 | 5/2018 | Ishikawa |
| 2018/0199837 A1 | 7/2018 | Aumer et al. |

FOREIGN PATENT DOCUMENTS

| | | |
|---|---|---|
| CN | 201438747 | 4/2010 |
| DE | 3910749 | 10/1990 |
| EP | 1297784 | 4/2003 |
| EP | 1480278 | 11/2004 |
| EP | 1480278 | 8/2006 |
| EP | 1908401 A1 | 4/2008 |
| EP | 2077091 | 7/2009 |
| EP | 2182839 | 5/2010 |
| EP | 1297784 | 9/2010 |

(56) References Cited

FOREIGN PATENT DOCUMENTS

| | | |
|---|---|---|
| EP | 1480278 | 6/2013 |
| EP | 2667769 A2 | 12/2013 |
| GB | 2408209 | 5/2005 |
| GB | 2411719 | 9/2005 |
| JP | 07241279 | 9/1995 |
| JP | 09253062 | 9/1997 |
| JP | 09299342 | 11/1997 |
| JP | 2000-116611 | 4/2000 |
| JP | 2001-025462 | 1/2001 |
| JP | 2003-159221 | 6/2003 |
| JP | 2004-513750 | 5/2004 |
| JP | 2004-283523 | 10/2004 |
| JP | 2005-040261 | 2/2005 |
| JP | 2005-270544 | 10/2005 |
| JP | 2007-044203 | 2/2007 |
| JP | 2007-185348 | 7/2007 |
| JP | 2008-136556 | 6/2008 |
| JP | 2008-279061 | 11/2008 |
| JP | 2009-153664 | 7/2009 |
| JP | 2010-526646 | 8/2010 |
| JP | 2014-068733 | 4/2014 |
| KR | 20-0204510 | 11/2000 |
| WO | 00/24064 | 4/2000 |
| WO | 00/47108 | 8/2000 |
| WO | 01/08552 | 2/2001 |
| WO | 02/17782 | 3/2002 |
| WO | 2005/010568 | 2/2005 |
| WO | 2005/020121 | 3/2005 |
| WO | 2005/036212 | 4/2005 |
| WO | 2005/110238 | 11/2005 |
| WO | 2006/009830 | 1/2006 |
| WO | 2006/067690 | 6/2006 |
| WO | 2007/012931 | 2/2007 |
| WO | 2007/053146 | 5/2007 |
| WO | 2008/141306 | 11/2008 |
| WO | 2011/127063 | 10/2011 |
| WO | 2013/019494 | 2/2013 |
| WO | 2013/038296 | 3/2013 |
| WO | 2013/109389 | 7/2013 |
| WO | 2013/109390 | 7/2013 |
| WO | 2014/092932 | 6/2014 |
| WO | 2014/196119 | 12/2014 |
| WO | 2015/068066 | 5/2015 |
| WO | 2015/128226 | 9/2015 |
| WO | 2015/131065 | 9/2015 |
| WO | 2017/027551 | 2/2017 |

OTHER PUBLICATIONS

Bifulco et al. "Bluetooth Portable Device for Continuous ECG and Patient Motion Monitoring During Daily Life" Medicon 2007 IFMBE Proceedings 16:369-372 (2007).

Brodersen et al. "In-Ear Acquisition of Vital Signs Discloses New Chances for Preventive Continuous Cardiovascular Monitoring" 4th International Workshop on Wearable and Implantable Body Sensor Networks 13:189-194 (2007).

Celka et al. "Motion Resistant Earphone Located Infrared based Heart Rate Measurement Device" Proceedings of the Second IASTED International Conference on Biomedical Engineering (pp. 582-585) (Feb. 16-18, 2004).

Comtois "Implementation of Accelerometer-Based Adaptive Noise Cancellation in a Wireless Wearable Pulse Oximeter Platform for Remote Physiological Monitoring and Triage" Thesis, Worcester Polytechnic Institute (149 pages) (Aug. 31, 2007).

Comtois et al. "A Comparative Evaluation of Adaptive Noise Cancellation Algorithms for Minimizing Motion Artifacts in a Forehead-Mounted Wearable Pulse Oximeter" Proceedings of the 29th Annual International Conference of the IEEE EMBS (pp. 1528-1531) (Aug. 23-26, 2007).

Comtois et al. "A Wearable Wireless Reflectance Pulse Oximeter for Remote Triage Applications" IEEE (pp. 53-54) (2006).

Duun et al. "A Novel Ring Shaped Photodiode for Reflectance Pulse Oximetry in Wireless Applications" IEEE Sensors 2007 Conference (pp. 596-599) (2007).

European Office Action corresponding to European Application No. 12820308.0 (5 pages) (dated Feb. 3, 2016).

Extended European Search Report corresponding to European Application No. 12820308.0 (6 pages) (dated Apr. 30, 2015).

Extended European Search Report corresponding to European Application No. 17169569.5 (7 pages) (dated Aug. 29, 2017).

Fitrainer "The Only Trainer You Need" http://itami.com © 2008 FiTrainer™ (2 pages) (Downloaded Feb. 26, 2010).

Fleming et al. "A Comparison of Signal Processing Techniques for the Extraction of Breathing Rate from the Photoplethysmorgram" World Academy of Science, Engineering and Technology 30:276-280 (Oct. 2007).

Fukushima et al. "Estimating Heart Rate using Wrist-type Photoplethysmography and Acceleration sensor while running" Conf Proc IEEE Eng Med Biol Soc. (pp. 2901-2904) (Sep. 2012).

Geun et al. "Measurement Site and Applied Pressure Consideration in Wrist Photoplethysmography" The 23rd International Technical Conference on Circuits/Systems, Computers and Communications (pp. 1129-1132) (2008).

Gibbs et al. "Active motion artifact cancellation for wearable health monitoring sensors using collocated MEMS accelerometers" Proc. of SPIE Smart Structures and Materials, 2005: Sensors and Smart Structures Technologies for Civil, Mechanical, and Aerospace Systems 5765:811-819 (2005).

Gibbs et al. "Reducing Motion Artifact in Wearable Bio-Sensors Using MEMS Accelerometers for Active Noise Cancellation" 2005 American Control Conference 1581-1586 (Jun. 8-10, 2005).

Haahr et al. "A Wearable "Electronic Patch" for Wireless Continuous Monitoring of Chronically Diseased Patients" Proceedings of the 5th International Workshop on Wearable and Implantable Body Sensor Networks, in conjunction with The 5th International Summer School and Symposium on Medical Devices and Biosensors (pp. 66-70) (Jun. 1-3, 2008).

Han et al. "Artifacts in wearable photoplethysmographs during daily life motions and their reduction with least mean square based active noise cancellation method" Computers in Biology and Medicine 42:387-393 (Apr. 2012).

Han et al. "Development of a wearable health monitoring device with motion artifact reduced algorithm" International Conference on Control, Automation and Systems 2007 (ICCAS 2007) (pp. 1581-1584) (Oct. 17-20, 2007).

Jiang "Motion-Artifact Resistant Design of Photoplethysmograph Ring Sensor for Driver Monitoring" Thesis, Massachusetts Institute of Technology (62 pages) (Feb. 2004).

Kuzmina et al. "Compact multi-functional skin spectrometry set-up" Advanced Optical Materials, Technologies, and Devices, Proc. of SPIE 6596:65960T-1-65960T-6 (2007).

Lee et al. "A Mobile Care System With Alert Mechanism" IEEE Transactions On Information Technology In Biomedicine 11(5):507-517 (Sep. 2007).

Lee et al. "Respiratory Rate Detection Algorithms by Photoplethysmography Signal Processing" 30th Annual International IEEE EMBS Conference (pp. 1140-1143) (Aug. 20-24, 2008).

Lindberg et al. "Monitoring of respiratory and heart rates using a fibre-optic sensor" Med Biol Eng Comput 30 (5):533-537 (Sep. 1992).

Luprano "Sensors and Parameter Extraction by Wearable Systems: Present Situation and Future" pHealth 2008 (29 pages) (May 21, 2008).

Lygouras et al. "Optical-Fiber Finger Photo-Plethysmograph Using Digital Techniques" IEEE Sensors Journal 2 (1):20-25 (Feb. 2002).

Maguire et al. "The Design and Clinical Use of a Reflective Brachial Photoplethysmograph" Signals and Systems Research Group, National University of Ireland (13 pages) (Apr. 2002).

Mendelson et al. "Measurement Site and Photodetector Size Considerations in Optimizing Power Consumption of a Wearable Reflectance Pulse Oximeter" Proceedings of the 25th Annual International Conference of the IEEE EMBS (pp. 3016-3019) (Sep. 17-21, 2003).

(56) References Cited

OTHER PUBLICATIONS

Mendelson et al. "Noninvasive Pulse Oximetry Utilizing Skin Reflectance Photoplethysmography" IEEE Transactions on Biomedical Engineering 35(10):798-805 (Oct. 1988).
Nakajima et al. "Monitoring of heart and respiratory rates by photoplethysmography using a digital filtering technique" Med. Eng. Phys. 18(5):365-372 (Jul. 1996).
Notification Concerning Transmittal of International Preliminary Report on Patentability in corresponding PCT Application No. PCT/US2012/048079 (12 pages) (dated Mar. 25, 2014).
Notification of Transmittal of the International Search Report and the Written Opinion of the International Searching Authority, or the Declaration, in corresponding PCT Application No. PCT/US2012/048079 (15 pages) (dated Oct. 9, 2012).
Poh et al. "Motion Tolerant Magnetic Earring Sensor and Wireless Earpiece for Wearable Photoplethysmography" IEEE Transactions on Information Technology in Biomedicine 14(3):786-794 (May 2010).
Renevey et al. "Wrist-Located Pulse Detection Using IR Signals, Activity and Nonlinear Artifact Cancellation" IEEE EMBS (4 pages) (2001).
Rhee et al. "Artifact-Resistant Power-Efficient Design of Finger-Ring Plethysmographic Sensors" IEEE Transactions on Biomedical Engineering 48(7):795-805 (Jul. 2001).
Shaltis "Analysis and Validation of an Artifact Resistant Design for Oxygen Saturation Measurement Using Photo Plethysmographic Ring Sensors" Thesis, Massachusetts Institute of Technology (103 pages) (Jun. 2004).
Shaw et al. "Warfighter Physiological and Environmental Monitoring: A Study for the U.S. Army Research Institute in Environmental Medicine and the Soldier Systems Center" Massachusetts Institute of Technology Lincoln Laboratory (141 pages) (Nov. 1, 2004).
Shin et al. "A Novel Headset with a Transmissive PPG Sensor for Heart Rate Measurement" 13th International Conference on Biomedical Engineering (pp. 519-522) (2009).
Spigulis et al. "Wearable wireless photoplethysmography sensors" Proc. of SPIE 6991:69912O-1-69912O-7 (2008).
Takatani et al. "Optical Oximetry Sensors for Whole Blood and Tissue" IEEE Engineering in Medicine and Biology (pp. 347-357) (Jun./Jul. 1994).
Vogel et al. "A System for Assessing Motion Artifacts in the Signal of a Micro-Optic In-Ear Vital Signs Sensor" 30th Annual International IEEE EMBS Conference (Aug. 20-24, 2008).
Vogel et al. "In-Ear Heart Rate Monitoring Using a Micro-Optic Reflective Sensor" Proceedings of the 29th Annual International Conference of the IEEE EMBS Cite Internationale (pp. 1375-1378) (Aug. 23-26, 2007).
Wang et al. "Multichannel Reflective PPG Earpiece Sensor With Passive Motion Cancellation" IEEE Transactions on Biomedical Circuitsand Systems 1(4):235-241 (Dec. 2007).
Wang et al. "Reflective Photoplethysmograph Earpiece Sensor for Ubiquitous Heart Rate Monitoring" 4th International Workshop on Wearable and Implantable Body Sensor Networks IFMBE Proceedings 13:179-183 (2007).
Webster, John G. "Design of Pulse Oximeters" Medical Science Series, Institute of Physics Publication (143 pages) (Aug. 1997).
Wei et al. "A New Wristband Wearable Sensor Using Adaptive Reduction Filter to Reduce Motion Artifact" Proceedings of the 5th International Conference on Information Technology and Application in Biomedicine, in conjunction with The 2nd International Symposium & Summer School on Biomedical and Health Engineering (pp. 278-281) (May 30-31, 2008).
Wikipedia "Least mean squares filter" Retrieved at URL: https://en.wikipedia.org/wiki/Least_mean_squares_filter (6 pages) (Retrieved on Mar. 17, 2016).
Wood "Motion Artifact Reduction for Wearable Photoplethysmogram Sensors Using Micro Accelerometers and Laguerre Series Adaptive Filters" Thesis, Massachusetts Institute of Technology (74 pages) (Jun. 2008).
Wood et al. "Active Motion Artifact Reduction for Wearable Sensors Using Laguerre Expansion and Signal Separation" Proceedings of the 2005 IEEE Engineering in Medicine and Biology 27th Annual Conference (pp. 3571-3574) (Sep. 1-4, 2005).

\* cited by examiner

SYSTEMS AND METHODS FOR VARIABLE FILTER ADJUSTMENT BY HEART RATE METRIC FEEDBACK

CROSS REFERENCE TO RELATED APPLICATION

This application is a continuation application of and claims priority from U.S. patent application Ser. No. 15/784,960, filed on Oct. 16, 2017, now U.S. Pat. No. 10,512,403, which is a continuation application of and claims priority from U.S. patent application Ser. No. 14/124,465, filed on Dec. 6, 2013, now U.S. Pat. No. 9,801,552, which is a 35 U.S.C. § 371 national stage application of PCT International Application No. PCT/US2012/048079, filed Jul. 25, 2012, which itself claims the benefit of provisional Patent Application No. 61/514,099, filed Aug. 2, 2011, entitled Systems and Methods for Variable Filter Adjustment by Physiological Metric Feedback, assigned to the assignee of the present invention, the disclosures of which are hereby incorporated herein by reference in their entirety as if set forth fully herein.

BACKGROUND

Various embodiments described herein relate generally to signal processing systems and methods, and more particularly to physiological signal processing systems and methods.

There is a growing market demand for personal health and environmental monitors, for example, for gauging overall health, fitness, metabolism, and vital status during exercise, athletic training, work, public safety activities, dieting, daily life activities, sickness and physical therapy. These personal health and environmental monitors process physiological signals that may be obtained from one or more physiological sensors, and are configured to extract one or more physiological metrics from physiological waveforms. Unfortunately, inaccurate physiological metric extraction can reduce the accuracy of health, fitness and/or vital status monitoring.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Various embodiments described herein can provide physiological signal processing systems for physiological waveforms that include cardiovascular signal components therein. These physiological signal processing systems may include a variable high pass filter that is responsive to the physiological waveform and that is configured to high pass filter the physiological waveform in response to a corner frequency that is applied thereto. A heart rate metric extractor is responsive to the variable high pass filter and is configured to extract a heart rate metric from the physiological waveform that is high pass filtered. A corner frequency adjustor is responsive to the heart rate metric extractor and is configured to determine the corner frequency that is applied to the variable high pass filter, based on the heart rate metric that was extracted. A physiological metric assessor may also be provided that is responsive to the heart rate metric extractor and that is configured to process the heart rate metric to generate at least one physiological assessment.

Physiological waveforms may be processed according to various embodiments described herein. For example, the physiological waveform may include an electroencephalogram (EEG), an electrocardiogram (ECG) and/or a radio frequency (RF) waveform, an electro-optical physiological waveform including a photoplethysmograph (PPG) waveform, an electro-photoacoustic waveform including a photoacoustic waveform, an electro-mechanical physiological waveform including an auscultation waveform, a piezo sensor waveform and/or an accelerometer waveform, and/or an electro-nuclear physiological waveform. Moreover, various physiological assessments may be provided including ventilator threshold, lactate threshold, cardiopulmonary status, neurological status, aerobic capacity ($VO_2$ max) and/or overall health or fitness.

Various configurations of variable high pass filters may also be provided according to various embodiments described herein. For example, the variable high pass filter may comprise a single high pass filter having an adjustable corner frequency, wherein the corner frequency adjustor is configured to determine the adjustable corner frequency. Alternatively, the variable high pass filter may comprise a plurality of high pass filters, a respective one of which includes a different value of the corner frequency, wherein the corner frequency adjustor is configured to select one of the plurality of high pass filters that corresponds to the corner frequency that is determined.

Various other embodiments of variable high pass filters may also be provided. Analog variable high pass filters may be provided with adjustable component values thereof. Alternatively, the variable high pass filter may comprise a variable digital high pass filter having a plurality of delay taps, wherein the corner frequency corresponds to a number of the plurality of delay taps that are selected to filter the physiological waveform. In these embodiments, the corner frequency adjuster may comprise a mapping system that is configured to map the heart rate metric that is extracted from the physiological waveform that is filtered into the number of the delay taps that are selected to high pass filter the physiological waveform.

Various embodiments described herein can also configure the corner frequency adjuster to reduce or prevent locking on an erroneous heart rate metric. In some embodiments, the corner frequency adjuster is configured to initially set a predetermined corner frequency corresponding to a predetermined heart rate prior to determining the corner frequency that is applied to the variable high pass filter from the heart rate metric. The predetermined heart rate may be a resting heart rate, such as 72 beats per minute. The corner frequency adjuster may also be configured to initially set the predetermined corner frequency corresponding to the predetermined heart rate until the heart rate metric extractor locks on a heart rate of the physiological waveform. Moreover, the corner frequency adjuster may also be configured to reset or reapply the predetermined corner frequency corresponding to the predetermined heart rate in response to determining that the physiological sensor is no longer responsive to a source of the physiological waveform. The corner frequency adjuster may also be configured to determine the at least one corner frequency that is applied to the variable high pass filter from the heart rate metric by applying a margin to the heart rate metric. Moreover, the variable high pass filter may include a gradual filter transition band (i.e., it is not a brick wall filter).

Various embodiments described herein may also provide physiological signal processing systems that may be used with physiological sensors that are configured to generate a physiological waveform that includes cardiovascular and pulmonary signal components therein. A variable high pass filter and a variable low pass filter are provided that are responsive to the physiological waveform and that are configured to high pass and low pass filter, respectively, the physiological waveform in response to at least one corner frequency that is applied thereto. A heart rate metric extractor is provided that is responsive to the variable high pass filter and that is configured to extract a heart rate metric from the physiological waveform that is filtered by the variable high pass filter. A respiration rate metric extractor is provided that is responsive to the variable low pass filter and that is configured to extract a respiration rate metric from the physiological waveform that is filtered by the variable low pass filter. A corner frequency adjustor is also provided that is responsive to the heart rate metric extractor and that is configured to determine the at least one corner frequency that is applied to the variable high pass filter and the variable low pass filter from the heart rate metric.

The variable high pass and the variable low pass filter may respectively comprise a single high pass and a single low pass filter having an adjustable corner frequency, and the corner frequency adjustor may be configured to determine the adjustable corner frequency for the single high pass filter and the single low pass filter. Alternatively, the variable high pass filter and the variable low pass filter may respectively comprise a plurality of high pass filters and a plurality of low pass filters, a respective one of which includes a different corner frequency, and the corner frequency adjustor may be configured to select one of the plurality of high pass filters and one of the plurality of low pass filters that corresponds to the at least one corner frequency that is determined by the corner frequency adjustor.

Moreover, in some embodiments, the variable high pass filter and the variable low pass filter comprise a variable digital high pass filter and a variable digital low pass filter having a plurality of high pass and low pass delay taps, respectively, and the corner frequency is determined by a number of the high pass and low pass delay taps that are selected to filter the physiological waveform.

The corner frequency adjuster may also comprise a mapping system that is configured to map the heart rate metric that is extracted from the physiological waveform that is filtered into the number of the delay taps that are selected to filter the physiological waveform. The mapping system may be configured to determine a corner frequency of the variable low pass filter and the variable high pass filter by determining a maximum of a minimum heart rate and the heart rate metric minus a margin, and may be further configured to determine the number of delay taps by rounding a product of the delay of the delay taps and the minimum heart rate divided by the corner frequency that was determined. Moreover, the mapping system may be configured to determine a corner frequency of the variable low pass filter and the variable high pass filter by applying a margin to the heart rate metric, and may be further configured to determine the number of delay taps from the corner frequency that was determined.

Various embodiments described herein can also configure the corner frequency adjuster to reduce or prevent locking on an erroneous heart rate metric. In some embodiments, the corner frequency adjuster is configured to initially set at least one predetermined corner frequency corresponding to a predetermined heart rate prior to determining the at least one corner frequency that is applied to the variable high pass filter and the variable low pass filter from the heart rate metric. The predetermined heart rate may be a resting heart rate, such as 72 beats per minute. The corner frequency adjuster may be configured to initially set the at least one predetermined corner frequency corresponding to the predetermined heart rate until the heart rate metric extractor locks on a heart rate in the physiological waveform. The corner frequency may also be configured to reset or reapply the at least one predetermined corner frequency corresponding to the predetermined heart rate in response to determining that the physiological sensor is no longer responsive to a source of the physiological waveform. The corner frequency adjuster may be configured to determine the corner frequency that is applied to the variable high pass filter and the variable low pass filter from the heart rate metric by applying a margin to the heart rate metric. Moreover, the variable high pass filter may include a gradual filter transition band (i.e., it is not a brick wall filter).

In any of the embodiments described herein, the corner frequency adjuster may include hysteresis to reduce or prevent excessive filter adjustment. Moreover, in any of these embodiments, the at least one corner frequency may comprise a same corner frequency that is applied to the variable high pass and low pass filters. Finally, in any of these embodiments, the sensor may be a plethysmograph sensor and, more specifically, a photoplethysmograph sensor.

Various embodiments have been described above in connection with physiological signal processing systems. However, analogous physiological signal processing methods may also be provided according to various embodiments described herein. For example, some embodiments described herein can provide a physiological signal processing method comprising high pass filtering the physiological waveform in response to an adjustable high pass filter corner frequency, extracting a heart rate metric from the physiological waveform that is high pass filtered and determining the adjustable high pass filter corner frequency that is applied to the high pass filtering, from the heart rate that was extracted. Moreover, the determining may be provided by selecting one of a plurality of high pass filters that corresponds to the high pass filter corner frequency that is determined, or determining a number of a plurality of delay taps that are selected in the filtering. Other embodiments corresponding to the above described system embodiments also may be provided.

Yet other embodiments of physiological signal processing methods comprise obtaining a physiological waveform that includes cardiovascular and pulmonary signal components therein, variable high pass and low pass filtering the physiological waveform in response to at least one corner frequency, extracting a heart rate metric from the physiological waveform that is filtered by the variable high pass filtering, extracting a respiration rate metric from the physiological waveform that is filtered by the variable low pass filtering, and determining the at least one corner frequency that is applied to the variable high pass and low pass filtering from the heart rate metric that was extracted. Again, the determining may comprise adjusting the corner frequency for the variable high pass and low pass filtering, for example by selecting one of a plurality of high pass and low pass filters that corresponds to at least one corner frequency that is determined and/or determining a number of a plurality of high pass and low pass delay taps that are selected by the variable high pass and low pass filtering. Specifically, the heart rate metric may be mapped into the number of delay taps. This may be embodied, for example, by determining a corner frequency of the variable low pass and the variable high pass filtering by applying a margin to the heart rate metric and determining the number of delay taps from the corner frequency. Other embodiments corresponding to the above described system embodiments may also be provided.

DETAILED DESCRIPTION

Figure 1:
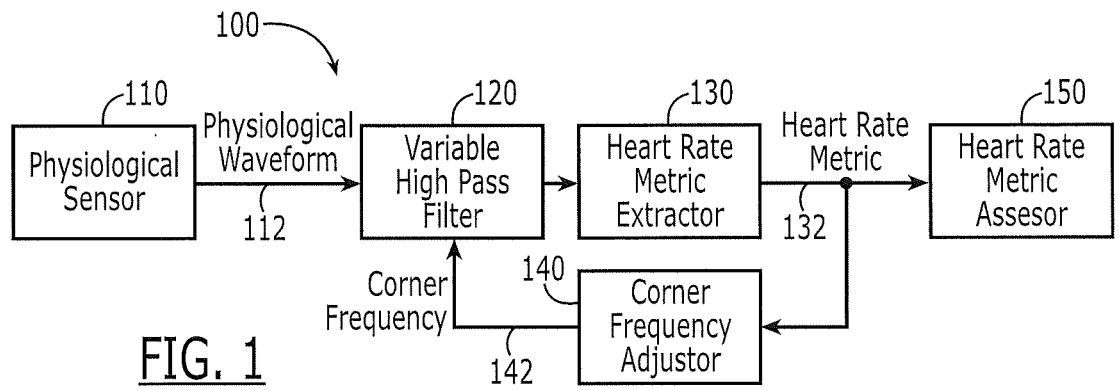
FIGS. 1-4 are functional block diagrams of physiological signal processing systems and methods according to various embodiments described herein.

The present invention will now be described more fully hereinafter with reference to the accompanying figures, in which various embodiments are shown. This invention may, however, be embodied in many different forms and should not be construed as limited to the embodiments set forth herein. Like numbers refer to like elements throughout. The sequence of operations (or steps) is not limited to the order presented in the figures and/or claims unless specifically indicated otherwise. Features described with respect to one figure or embodiment can be associated with another embodiment or figure although not specifically described or shown as such.

It will be understood that, when a feature or element is referred to as being "connected", "attached", "coupled" or "responsive" to another feature or element, it can be directly connected, attached, coupled or responsive to the other feature or element or intervening features or elements may be present. In contrast, when a feature or element is referred to as being "directly connected", "directly attached", "directly coupled" or "directly responsive" to another feature or element, there are no intervening features or elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets as described herein may include mono headsets (one earbud) and stereo headsets (two earbuds), earbuds, hearing aids, ear jewelry, face masks, headbands, and the like.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of embodiments of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) who may wear a headset incorporating embodiments of the present invention.

In the included figures, various embodiments will be illustrated and described. However, it is to be understood that embodiments of the present invention are not limited to those worn by humans.

The ear is an ideal location for wearable health and environmental monitors. The ear is a relatively immobile platform that does not obstruct a person's movement or vision. Headsets located at an ear have, for example, access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Wireless, Bluetooth®-enabled, and/or other personal communication headsets may be configured to incorporate physiological and/or environmental sensors, according to some embodiments of the present invention. As a specific example, Bluetooth® headsets are typically lightweight, unobtrusive devices that have become widely accepted socially. Moreover, Bluetooth® headsets are cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of headsets include, but are not limited to accelerometers, auscultatory sensors, pressure sensors, humidity sensors, color sensors, light intensity sensors, pressure sensors, etc.

Optical coupling into the blood vessels of the ear may vary between individuals. As used herein, the term "coupling" refers to the interaction or communication between excitation light entering a region and the region itself. For example, one form of optical coupling may be the interaction between excitation light generated from within a light-guiding earbud and the blood vessels of the ear. Light guiding earbuds are described in co-pending U.S. Patent Application Publication No. 2010/0217102, which is incorporated herein by reference in its entirety. In one embodiment, this interaction may involve excitation light entering the ear region and scattering from a blood vessel in the ear such that the intensity of scattered light is proportional to blood flow within the blood vessel. Another form of optical coupling may be the interaction between excitation light generated by an optical emitter within an earbud and the light-guiding region of the earbud.

Various embodiments described herein are not limited to headsets that communicate wirelessly. In some embodiments of the present invention, headsets configured to monitor an individual's physiology and/or environment may be wired to a device that stores and/or processes data. In some embodiments, this information may be stored on the headset itself. Furthermore, various embodiments described herein are not limited to earbuds. Some embodiments may be employed around another part of the body, such as a digit, finger, toe, limb, wrist, around the nose or earlobe, or the like. Other embodiments may be integrated into a patch, such as a bandage that sticks on a person's body.

Various embodiments described herein may arise from recognition that a physiological signal component in a physiological waveform may change dramatically over time, for example due to the user's activity level and/or other factors. In order to effectively extract a physiological metric from the physiological waveform, the physiological metric itself may be used to directly or indirectly adjust a parameter of a variable filter, such as a filter's low pass or high pass corner frequency. Accordingly, accurate filtering may be provided and accurate parameter extraction may be obtained, notwithstanding the large changes that may take place in the value of the physiological metric.

It also may be exceedingly difficult to extract metrics from physiological sensors that generate physiological waveforms that include multiple physiological signal components therein. For example, a physiological sensor, such as a plethysmograph or a photoplethysmograph, may include cardiovascular and pulmonary signal components therein. Unfortunately, these physiological metrics have overlapping frequency ranges. For example, the cardiovascular signal component (heart rate) may range from about 45 beats per minute to about 220 beats per minute, while the pulmonary signal component (respiration rate) may range from about 12 breaths per minute to about 70 breaths per minute. Due to the overlap, it may be exceedingly difficult to separate the two physiological components.

However, various embodiments described herein may arise from further recognition that, in general, although heart rate and respiration rate may overlap, their rise and fall may generally track due to, for example, changes in physical activity or the environment. Thus, they may both generally go up together and go down together. Accordingly, various embodiments described herein can provide a variable high pass and a variable low pass filter having at least one corner frequency that can be varied in response to a heart rate metric that is extracted from the high pass filtered physiological waveform. By providing variable filter adjustment using physiological metric feedback, the heart and/or respiration rate may be extracted accurately, notwithstanding the fact that they are contained in the same signal and overlap in their frequency ranges.

Various embodiments described herein may also arise from recognition that it did not appear to be heretofore possible to use an extracted heart rate to control a high pass filter that feeds a heart rate metric extractor. Specifically, due to the possibility for the extracted heart rate to be in error, the high pass filter may blind the metric extractor from the heart rate frequency in the physiological waveform signal. In other words, the heart rate metric extractor may get stuck at a high rate and, due to the high pass filtering that takes place, may never become responsive to the heart rate in the physiological waveform. Accordingly, the heart rate metric extractor may diverge or run away from the actual heart rate. Yet, despite these potential problems, various embodiments described herein can allow an extracted heart rate metric to be used to set a variable high pass filter corner frequency, and in some embodiments to also set a variable low pass filter corner frequency, while reducing or eliminating the heart rate extractor from being blinded to its own frequency.

Accordingly, various embodiments described herein can reduce or prevent locking on an erroneous heart rate metric. Thus, a heart rate metric can be used to set a corner frequency of a variable high pass filter for heart rate extraction. Moreover, the heart rate metric that is extracted may also be used to set a corner frequency for a variable low pass filter for respiration rate extraction, according to various embodiments described herein.

FIG. 1 is a functional block diagram of physiological signal processing systems and methods according to various embodiments described herein. Referring now to FIG. 1, these physiological signal processing systems/methods 100 may be used to process a physiological waveform 112 that is produced by a physiological sensor 110, and that includes a physiological signal component therein. The physiological waveform 112 may include an electrical physiological waveform including an electroencephalogram (EEG), an electrocardiogram (ECG) and/or a radio frequency (RF) waveform, an electro-optical physiological waveform including a photoplethysmograph (PPG) waveform, an electro-photoacoustic waveform including a photoacoustic waveform, an electro-mechanical physiological waveform including an auscultation waveform, a piezo sensor waveform and/or an accelerometer waveform, and/or an electro-nuclear physiological waveform. The physiological signal component may include a neurological, cardiovascular and/or pulmonary signal component. For example, in some embodiments, the physiological sensor 110 may be a plethysmograph sensor, such as a photoplethysmograph (PPG) sensor, and the physiological waveform may include both cardiovascular and pulmonary signal components therein.

Still referring to FIG. 1, a heart rate metric extractor 130 extracts a heart rate metric 132 from the physiological waveform 112. The heart rate metric extractor 130 may extract the heart rate metric using one or more conventional techniques. Moreover, a heart rate metric assessor 150 may be provided to assess the heart rate metric according to one or many known physiological metric assessment techniques. The physiological assessment may include ventilator threshold, lactate threshold, cardiopulmonary status, neurological status, aerobic capacity ($VO_2$ max) and/or overall health or fitness.

Still referring to FIG. 1, the heart rate metric extractor 130 is coupled to the physiological sensor 110 by a variable high pass filter 120. The variable high pass filter 120 is responsive to the physiological sensor 110, and is configured to high pass filter the physiological waveform 112 in response to a corner frequency 142 that is applied thereto. The high pass filter 120 may include a single analog or digital high pass filter having an adjustable corner frequency 142. Alternatively, the variable high pass filter 120 may comprise a plurality of analog or digital high pass filters, a respective one of which includes a different value of the corner frequency 142. Moreover, depending on the physiological waveform that is processed, the variable filter may be a variable high pass, low pass, bandpass, notch and/or other filter, and the filter parameter may be a low pass filter corner frequency, a high pass filter corner frequency, a bandpass filter corner frequency and/or bandwidth and/or a notch frequency. The variable digital filter may be embodied by a plurality of delay taps, the number of which is selected to provide the variable filtering.

Still continuing with the description of FIG. 1, a corner frequency adjuster 140 is provided that is responsive to the heart rate metric extractor 130 and is configured to determine the corner frequency 142 that is applied to the variable high pass filter 120 based on the heart rate metric 132 that was extracted. Accordingly, variable filter adjustment by physiological metric feedback is provided.

Many embodiments of corner frequency adjusters 140 will be described in detail below. In general, the corner frequency adjuster 140 may be configured to determine a corner frequency that is applied to the variable high pass filter 120 or to select from among a plurality of variable high pass filters, for example by selecting a number of delay taps in a variable digital high pass filter. For example, as will be described in more detail below, the corner frequency adjuster 140 may include a mapping system that is configured to map the heart rate metric 132 that is extracted from the physiological waveform 112 that is filtered by the variable high pass filter 120, into a number of delay taps that is selected to filter the physiological waveform 112 by the variable high pass filter 120.

Figure 2:
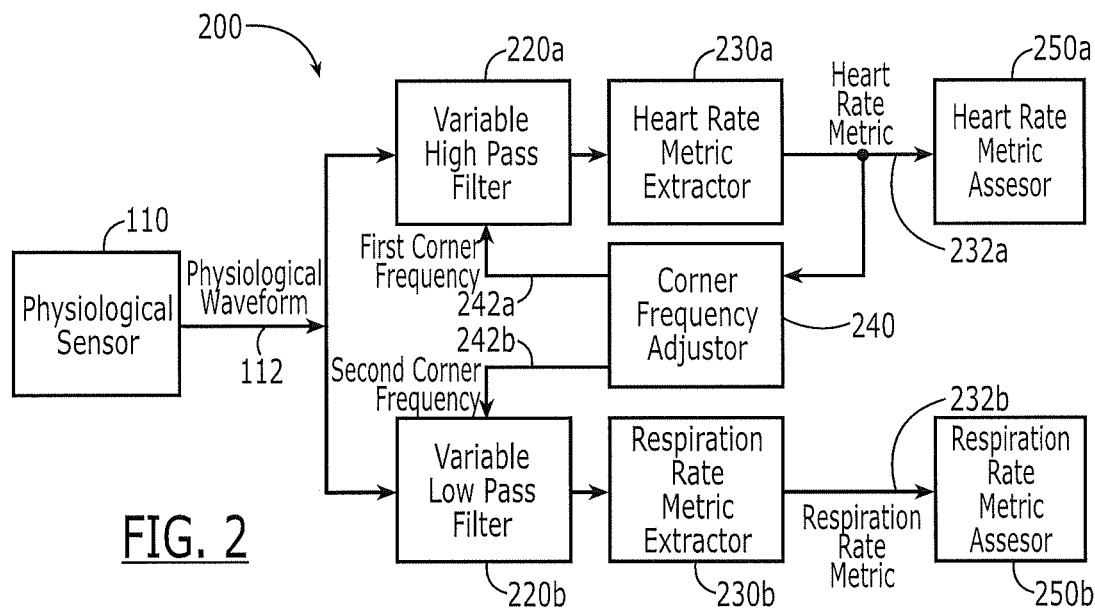

FIG. 2 is a functional block diagram of physiological signal processing systems and methods according to various other embodiments described herein. These physiological signal processing systems and methods 200 are configured to extract cardiovascular and pulmonary physiological signal components that are included in a physiological waveform 112 as provided by the physiological sensor 110. In some embodiments, the cardiovascular and pulmonary physiological signal components rise and fall in frequency roughly in tandem, and the cardiovascular signal component includes a highest frequency that is higher than the lowest frequency of the pulmonary signal component. It will be understood that more than two physiological signal components may be processed in other embodiments, but only two components are illustrated in FIG. 2 for ease of illustration.

In embodiments of FIG. 2, a variable high pass filter 220a and a variable low pass filter 220b may be provided. The variable high pass filter 220a is responsive to the physiological waveform 112 and is configured to high pass filter the physiological waveform in response to a first corner frequency 242a that is applied thereto. The variable low pass filter 220b is responsive to the physiological waveform 112 and is configured to low pass filter the physiological waveform in response to a second corner frequency 242b that is applied thereto. The first and second corner frequencies 242a, 242b may be identical in some embodiments, and may be different in other embodiments. Moreover, when the first physiological signal component is a cardiovascular signal component and the second physiological signal component is a pulmonary signal component, the first corner frequency 242a is a high pass corner frequency and the second corner frequency 242b is a low pass corner frequency.

Continuing with the description of FIG. 2, a heart rate metric extractor 230a and a respiration rate metric extractor 230b may be provided. The heart rate metric 232a may be processed and analyzed by a heart rate metric assessor 250a, and the respiration rate 232b may be processed and analyzed by a respiration rate metric assessor 250b. Many techniques for operating heart rate and respiration rate metric extractors and assessors are known, and need not be described further herein.

Still referring to FIG. 2, a corner frequency adjuster 240 is provided. The corner frequency adjuster 240 is responsive to the heart rate metric extractor 230a to determine the first and second corner frequencies 242a and 242b that are applied to the variable high pass and low pass filters 220a and 220b, respectively. Various embodiments of the corner frequency adjuster 240 may be provided. Various detailed examples will be provided below.

Figure 3:
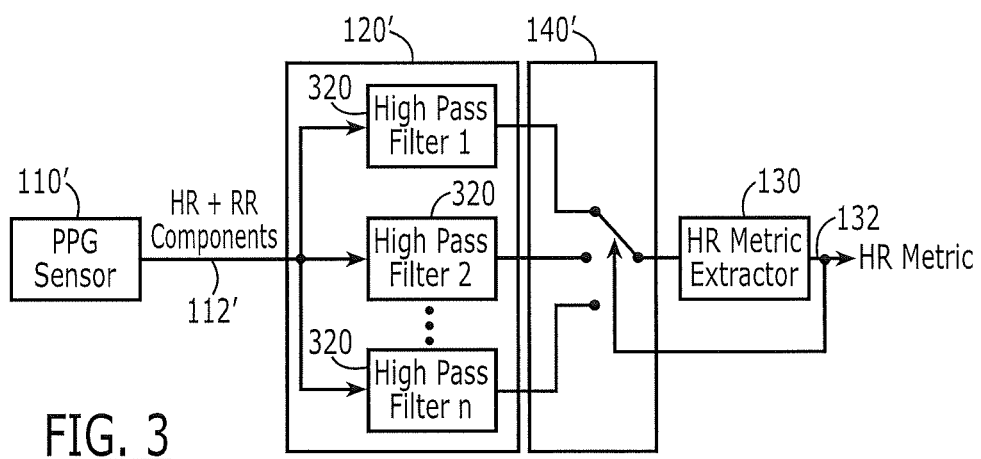

FIG. 3 is a functional block diagram of an embodiment of FIG. 1 that may be used to extract a heart rate metric 132 from the physiological waveform 112' that is produced by a PPG sensor 110', wherein the physiological waveform 112' includes both heart rate (HR) and respiration rate (RR) components. A variable high pass filter 120' is embodied in FIG. 3 by a plurality of high pass filters 320, each of which includes a different corner frequency. The heart rate metric extractor 130 is configured to extract a heart rate metric 132 using any known technique. The corner frequency adjuster 140 of FIG. 1 is embodied by a corner frequency adjuster 140', represented as a switch that is configured to select one of the plurality of high pass filters 320 that corresponds to the corner frequency that is determined. For example, in some embodiments, the corner frequency adjuster 140' uses a mapping function to select one of the plurality of high pass filters 320 that has a corner frequency that is within a margin of the heart rate metric 132'. In some embodiments, the margin may correspond to a margin of between about 18 and about 30 beats per minute below the heart rate metric 132'. By selecting the appropriate high pass filter 320, the corner frequency adjuster 140' can reduce or prevent the respiration rate component from interfering with the extraction of the heart rate component.

It will be understood that the margin may be selected as a function of the heart rate metric 132. For example, a table lookup may be used to map a heart rate metric 132 that is extracted into a desired high pass filter corner frequency, and then the filter 320 may be selected that has a corner frequency that is closest to the mapped corner frequency. It will also be understood that hysteresis may be used to reduce or prevent switching of the high pass filters 320 too rapidly, because the rapid switching may adversely affect the extraction of the heart rate metric by the heart rate metric extractor 130.

In other embodiments of FIG. 3, it may also be desirable to extract a respiration rate metric from the waveform 112', so that low pass filters may be used in addition to high pass filters 320. The corner frequency adjuster 140' may be configured to adjust low pass filter corner frequency by applying a given margin below the heart rate metric.

Figure 4:
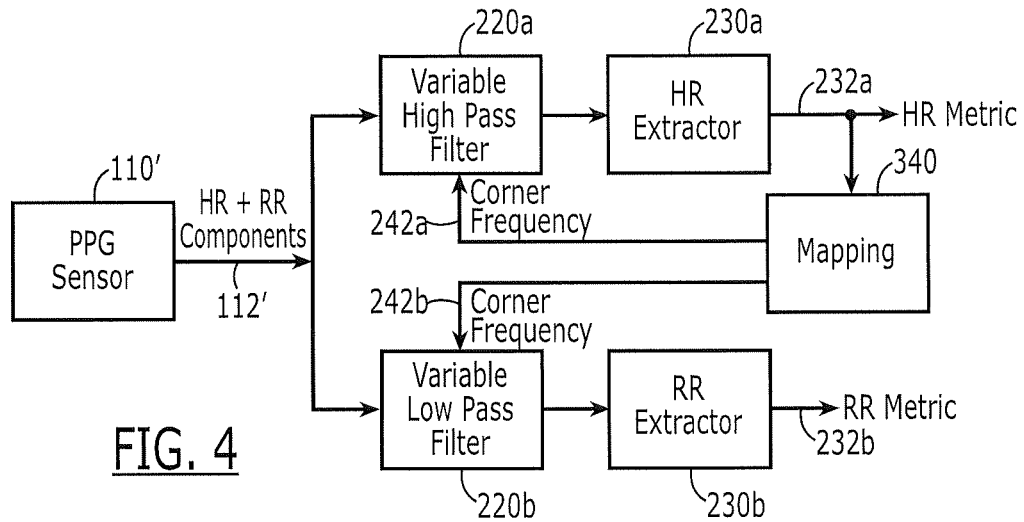

FIG. 4 is a more detailed functional block diagram of embodiments of FIG. 2, and may be used to extract a heart rate metric 232a and a respiration rate metric 232b from a PPG sensor 110' that provides a PPG sensor waveform 112' that includes both heart rate and respiration rate components. A variable high pass filter 220a and a variable low pass filter 220b is provided. Each of these filters may be embodied by a single filter with an adjustable corner frequency or by multiple filters having different corner frequencies, one of which may be selected. Heart rate extractor 230a and respiration rate extractor 230b are responsive to the variable high pass filter 220a and the variable low pass filter 220b, respectively, so as to obtain a heart rate metric 232a and a respiration rate metric 232b. The corner frequency adjuster previously described may be embodied by a mapping function 340. As shown in embodiments of FIG. 4, the mapping function 340 is responsive to the heart rate metric 232a and is responsible for determining both the high pass filter corner frequency 242a and the low pass filter corner frequency 242b. In some embodiments, the same corner frequency may be used for both the variable high pass filter 220a and the variable low pass filter 220b. In other embodiments, the mapping function 340 may determine different corner frequencies 242a and 242b.

In embodiments of FIG. 4, only the heart rate metric 232a is used by the mapping function to determine the corner frequency for both the variable high pass filter 220a and the variable low pass filter 220b. It has been found, according to various embodiments described herein, that the heart rate metric 232a may provide a more accurate basis for determining both corner frequencies, because the heart rate metric may be subject to less conscious control by the user compared to the respiration rate metric. A specific mapping function will be described below.

Figure 5:
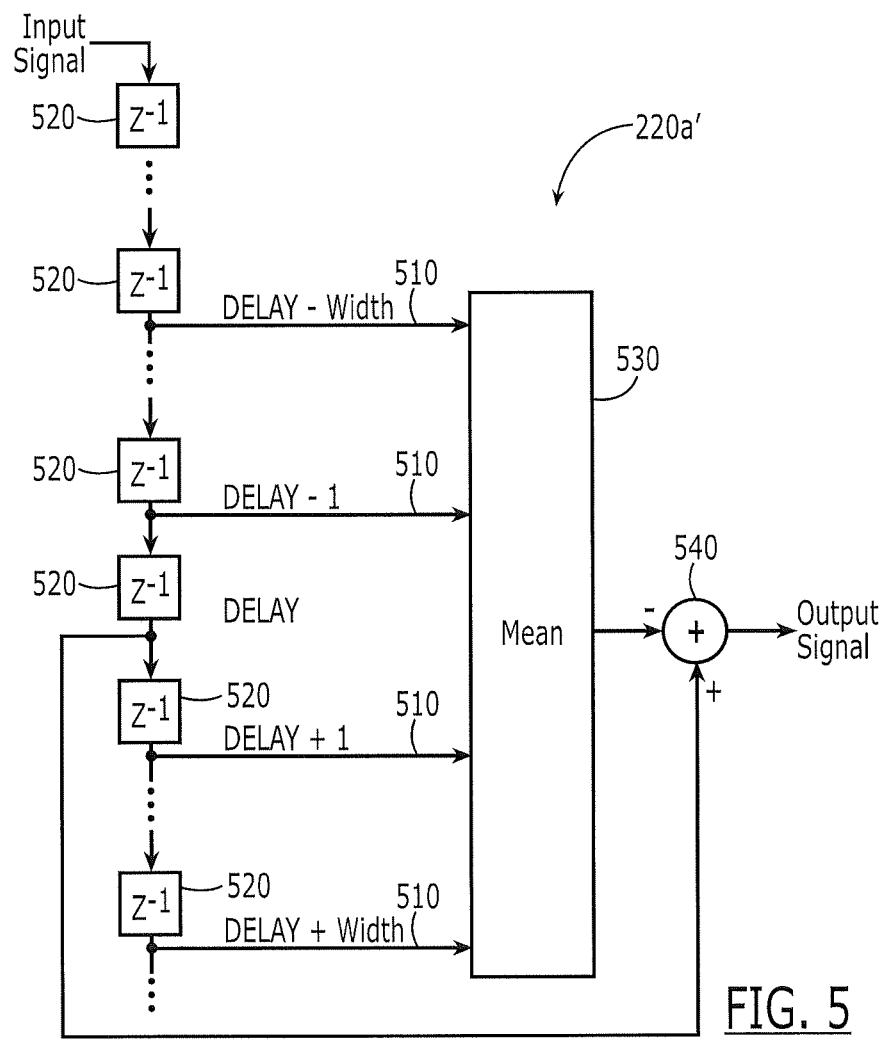
FIG. 5 is a functional block diagram of a digital variable high pass filter according to various embodiments described herein.

As was described above, the variable high pass filter 220a and/or the variable low pass filter 220b of FIG. 4 may comprise a variable digital high pass filter and/or a variable digital low pass filter. FIG. 5 illustrates an embodiment of a variable digital high pass filter, and FIG. 6 illustrates an embodiment of a variable digital low pass filter.

Referring to FIG. 5, these embodiments of a variable high pass filter 220a' include a plurality of high pass delay taps 510 that are generated by a plurality of digital delay elements 520. The digital delay elements 520 are responsive to an input signal, which may be the physiological waveform 112' of a PPG sensor, and the variable high pass filter 220a' provides an output signal, which may be provided to a metric extractor, such as an HR extractor 230a of FIG. 4. A "width" parameter determines the number of delay taps that are selected by a mean block 530 and a summing node 540, to determine the output signal. As shown in FIG. 6, the variable low pass filter 220b' can include a similar architecture. However, a summer 540 may not be needed in the variable low pass filter 220b' because the "DELAY" tap already feeds the mean block 530 with the same sign as the other taps 510.

Figure 6:
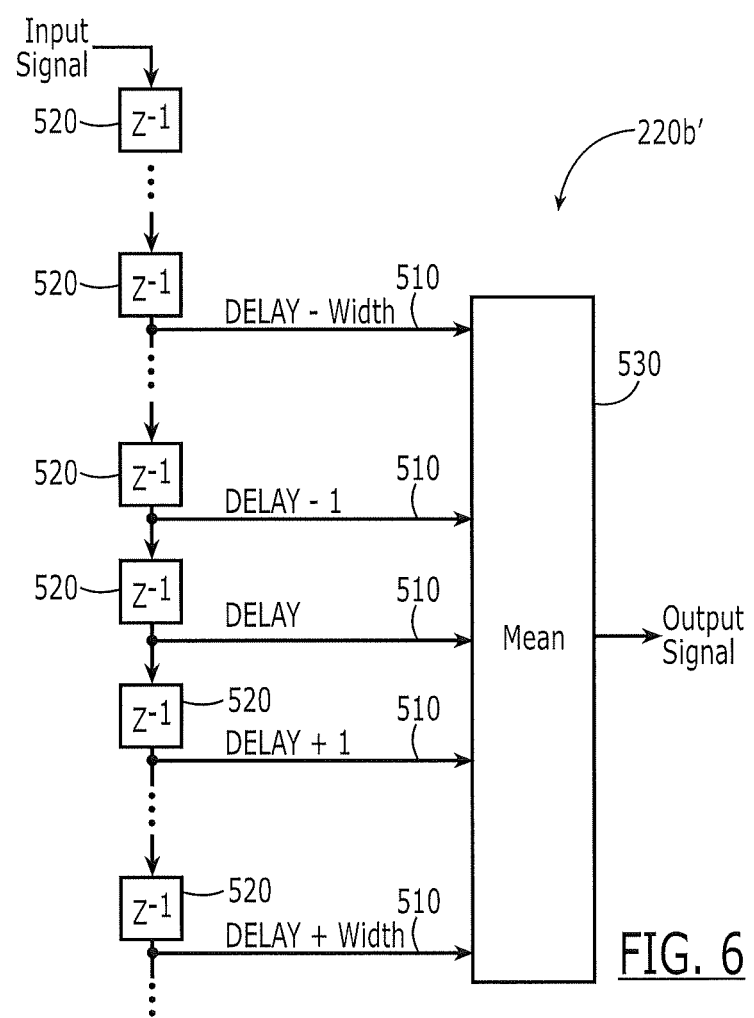
FIG. 6 is a functional block diagram of a digital variable low pass filter according to various embodiments described herein.

Accordingly, FIGS. 5 and 6 illustrate various embodiments wherein the variable high pass filter (FIG. 5) and/or the variable low pass filter (FIG. 6) comprises a variable digital high pass filter 220a' and/or a variable digital low pass filter 220b' having a plurality of high pass and/or low pass delays taps 510, respectively, wherein the corner frequency is determined by a number of high pass and/or low pass delay taps 510 that are selected to filter the physiological waveform.

A specific embodiment of a mapping function 340 will now be described. In these embodiments, the mapping function 340 is configured to determine a corner frequency 242a of the variable high pass filter 220a' and the corner frequency 242b of the variable low pass filter 220b' by applying a margin to the heart rate metric 232a, and is further configured to determine the number of delay taps 510 from the corner frequency that was determined.

A mathematical description of this mapping function 340 may be provided by Equations (1) and (2):

$$\text{CornerFreq}=\max(\text{MINIMUM\_HR\_BPM},\text{HeartRate}-\text{MARGIN\_BPM}) \quad (1)$$

$$\text{Width}=\text{round}(\text{DELAY}*\text{MINIMUM\_HR\_BPM}/\text{CornerFreq}) \quad (2)$$

In Equations (1) and (2), variables in CAPITAL_LETTERS are predetermined constants, while variables in CamelCase may change every frame. In this mapping function, CornerFreq is the corner frequency 242a and 242b. MINIMUM_HR_BPM is the minimum heart rate to be measured in beats per minute. HeartRate is the heart rate metric 232a that is measured. MARGIN_BPM is a desired margin between the reported heart rate and the corner frequency of the variable filter, which may be empirically determined. The margin allows for some error in the reported heart rate without causing significant attenuation by the variable high pass filter. Accordingly, in Equation (1) the corner frequency is determined by the maximum of either the minimum heart rate or the measured heart rate minus the margin that is set. Moreover, in Equation (2), Width is the parameter in FIGS. 5 and 6 that determines the number of delay taps 510. Specifically, in FIGS. 5 and 6, two times the width determines the number of delay taps that are input into the mean block 530. As shown in Equation (2), the width may be determined by rounding up or down the value of the delay of each of the delay elements 520 multiplied by the minimum heart rate divided by the corner frequency that was determined in Equation (1).

Accordingly, Equations (1) and (2) illustrate an embodiment wherein the mapping function 340 is configured to determine a corner frequency of the variable low pass filter

220b and the variable high pass filter 220a by determining a maximum of a minimum heart rate, and the heart rate metric 232a minus the margin, and is further configured to determine the number of delay taps 510 by rounding a product of the delay 520 of the delay taps 510 and the minimum heart rate divided by the corner frequency 242a/242b that was determined. It will be understood, however, that many other mapping functions may be provided according to other embodiments described herein.

Embodiments that were described above in connection with FIGS. 1-4 use a heart rate metric that was extracted to provide corner frequency adjustment of a variable high pass filter for a heart rate metric extractor, and may also use the heart rate metric that was extracted to adjust a corner frequency of a variable low pass filter of a respiration rate metric extractor. Heretofore, it does not appear that feedback of an extracted heart rate was used to control a high pass filter feeding a heart rate metric extractor. Specifically, because of the possibility for the extracted heart rate to be in error, the variable high pass filter may blind the heart rate metric extractor from the heart rate frequency in the physiological waveform. Stated differently, the heart rate metric extractor could lock on, i.e., get stuck at, a high rate, and remain unresponsive to the actual heart rate in the physiological waveform. Specifically, if the heart rate metric extractor locks on a high rate, the variable high pass filter may filter out the actual (lower) heart rate frequency in the physiological waveform. Accordingly, the heart rate metric extractor may diverge or run away from the actual heart rate. Thus, heretofore, feedback of the extracted heart rate to control the high pass filter feeding the heart rate metric extractor does not appear to have been used. In sharp contrast, various embodiments described herein can reduce or prevent locking on an erroneous heart rate metric. Thus, various embodiments described herein can use feedback of the heart rate metric that was extracted to control the high pass filter feeding the heart rate metric extractor, as was illustrated in FIGS. 1-4. The heart rate metric that was extracted may also be used to feed the low pass filter for the respiration rate metric extractor, as was shown in FIGS. 2 and 4.

Figure 7:
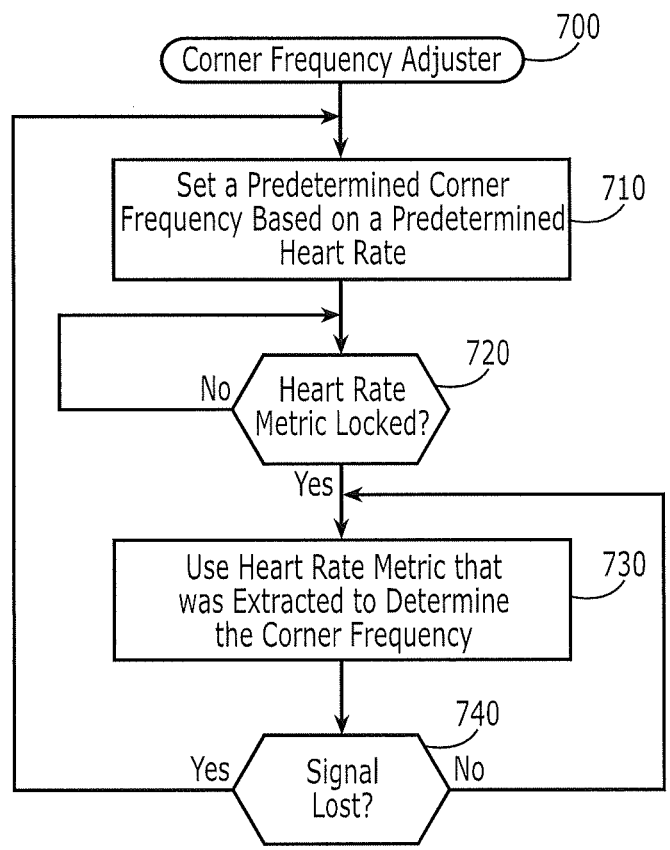
FIG. 7 is a flowchart of operations that may be performed by a corner frequency adjuster according to various embodiments described herein.

FIG. 7 is a flowchart of operations that may be performed by a corner frequency adjuster 700, such as the corner frequency adjuster 140 of FIG. 1, the corner frequency adjuster 240 of FIG. 2, the corner frequency adjuster 140' of FIG. 3, or the mapping function 340 of FIG. 4, to reduce or prevent an erroneous extracted heart rate from blinding the heart rate metric extractor to the heart rate frequency in the physiological waveform. Referring now to FIG. 7, the corner frequency adjuster 700 may be configured to initially set at least one predetermined corner frequency corresponding to a predetermined heart rate prior to determining the at least one corner frequency that is applied to the variable high pass filter, and in some embodiments to the variable low pass filter, from the heart rate metric, as illustrated at Block 710. Thus, at startup, the extracted heart rate 132 may be initialized to a predetermined, relatively low heart rate, such as a resting heart rate of, for example, 72 beats per minute. By initially setting the extracted heart 132 at a low value, subsequent blinding of the metric extractor by the high pass filter that is set for a high heart rate, may be reduced or prevented. Thus, the corner frequency adjuster 700 is configured to reduce or prevent locking on an erroneous heart rate in the physiological waveform.

Then, at Block 720, once a heart rate metric is locked, the heart rate metric that was extracted may be used to determine the corner frequency at Block 730. Thus, Blocks 710-730 illustrate the use of a "hunting mode" at startup, where the corner frequency of the high pass filter, and in some embodiments of the low pass filter, is set at a predetermined frequency (Block 710) until the heart rate metric extractor locks on the heart rate PPG signal at Block 720. Then, the heart rate metric that was extracted may be used at Block 730.

One way to determine that the heart rate metric extractor has locked on the heart rate in the physiological waveform at Block 720 is to determine when the physiological waveform spectral peak is within a window around the extracted heart rate. The window may be a predetermined window that remains constant, or may be a variable window. If the spectral peak is within the window around the extracted heart rate, the heart rate may be deemed to be believed, whereas if it is outside the window, it could be noise, and therefore be erroneous.

Finally, at Block 740, a determination may be made that the physiological waveform signal is lost, for example, because the physiological sensor 110 goes off the body. A determination that the physiological sensor goes off the body may be obtained using a proximity sensor and/or other techniques. If the signal is lost at Block 740, operations may return to Block 710 to reset (i.e., reapply) the predetermined heart rate and then return into hunting mode at Blocks 720 and 730. On the other hand, as long as the signal is not lost at Block 740, the heart rate metric that was extracted may continue to be used to determine the at least one corner frequency at Block 730. Thus, the corner frequency adjuster is configured to reduce or prevent locking on an erroneous heart rate metric.

Other techniques may also be used to reduce or prevent the high pass filter from blinding the metric extractor to the heart rate frequency in the physiological waveform. For example, the high pass filters 120, 220a, 120' or 220a' may all use a gradual filter transition band. Stated differently, brick wall high pass filters are not used in these embodiments. Thus, the gradual transition high pass filter may have a greater ability to include the heart rate frequency in the high pass filtered signal. Another technique may use a margin between the extracted heart rate and the corner frequency of the high pass filter. For example, 18 beats per minute margin may be used, as was already described. The above described techniques may be used individually, or in various combinations and subcombinations, to reduce or prevent the high pass filter from blinding the metric extractor from the heart rate frequency in the physiological waveform, and thereby reduce or prevent locking on an erroneous heart rate metric.

Figure 8:
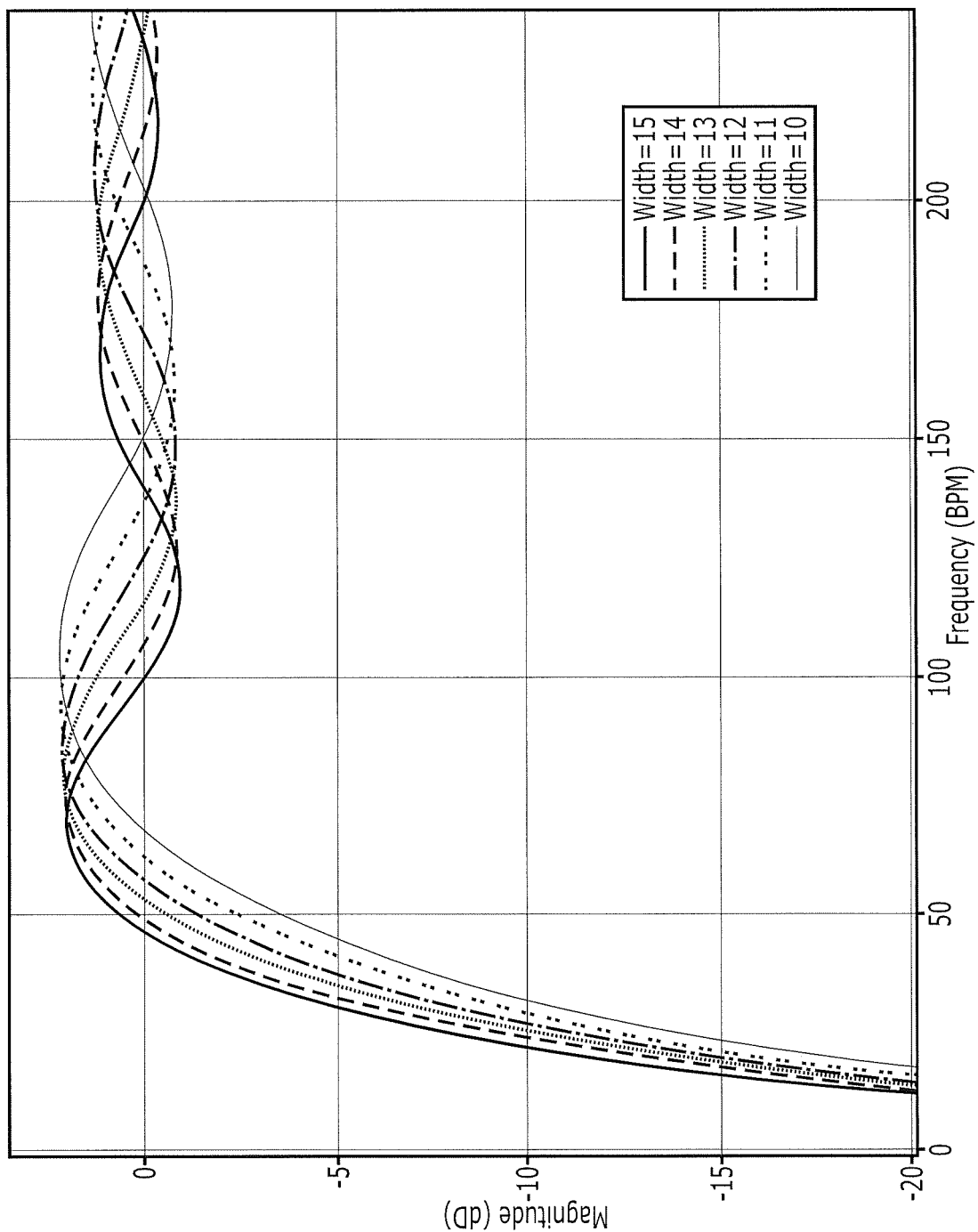
FIG. 8 graphically illustrates adjusting a corner frequency of a variable high pass filter according to various embodiments described herein.

FIG. 8 illustrates how the corner frequency of a variable high pass filter, such as the variable high pass filter 220a' of FIG. 5, may be varied using the mapping function 340 described by Equations (1) and (2) above, according to various embodiments described herein. FIG. 8 assumes a value of DELAY of 15 samples and plots the frequency response of the variable high pass filter 220a' with various width values from 10 to 15 at a sample rate of 25 Hz. As shown, the corner frequency of the variable high pass filter 220a', which may be measured at, for example, the −2 dB, −3 dB or −6 dB magnitude, can be varied by varying the width parameter. The high pass filter of FIG. 8 may be used to extract the heart rate metric 232a.

Figure 9:
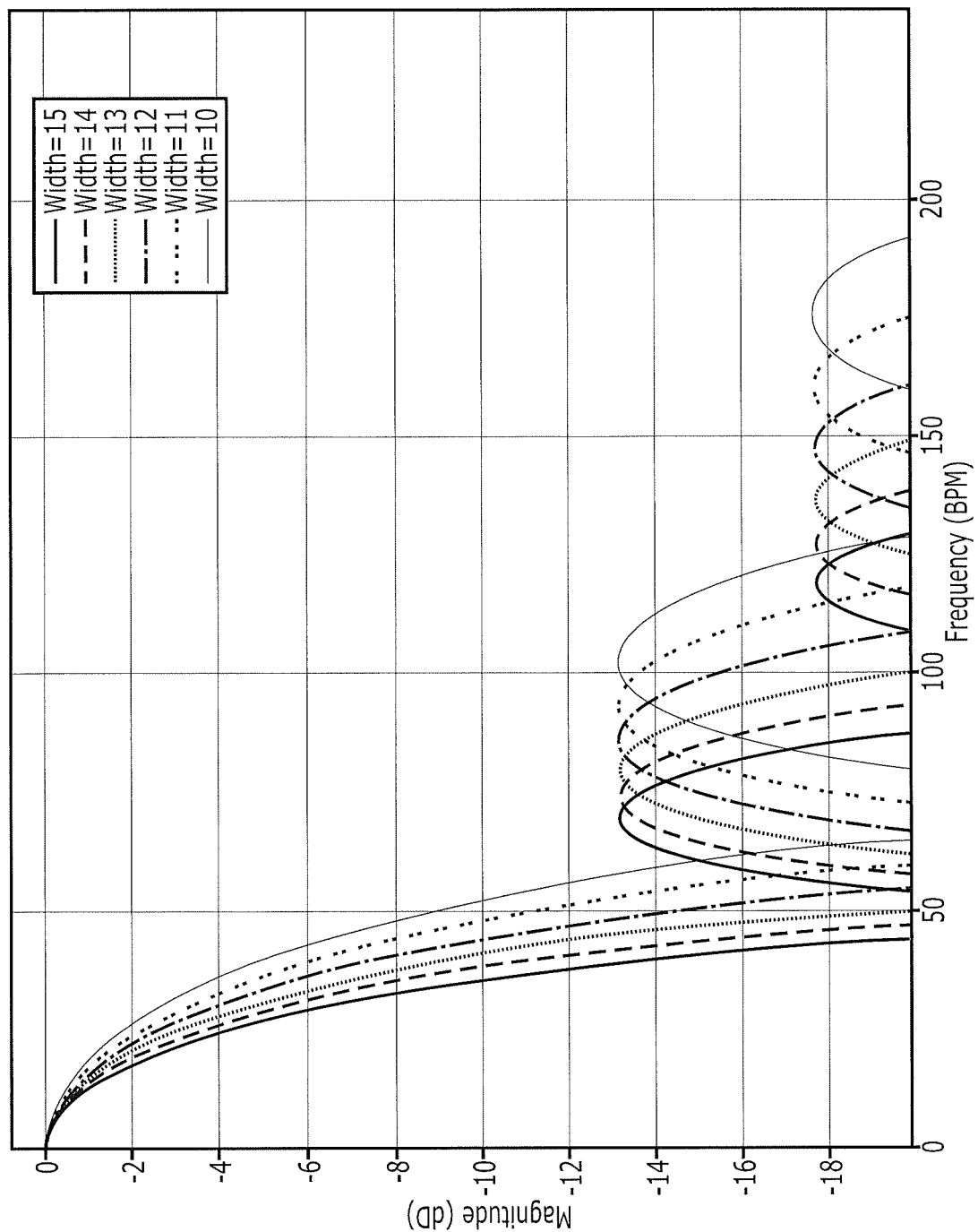
FIG. 9 graphically illustrates adjusting a corner frequency of a variable low pass filter according to various embodiments described herein.

FIG. 9 illustrates analogous operations for a variable digital low pass filter 220b', such as illustrated in FIG. 6. Again, in FIG. 9, a DELAY value of 15 samples is plotted as a function of widths from 10 to 15. The cutoff frequency may be measured, for example, by the −12 dB, −10 dB or −8 dB points in the magnitude. Accordingly, variable cutoff frequency low pass filters may be used to extract the respiration rate metric 232b.

FIGS. 10-15 illustrate other measured results. Specifically, FIG. 10 graphically illustrates a typical noise-reduced PPG spectrum.

Figure 10:
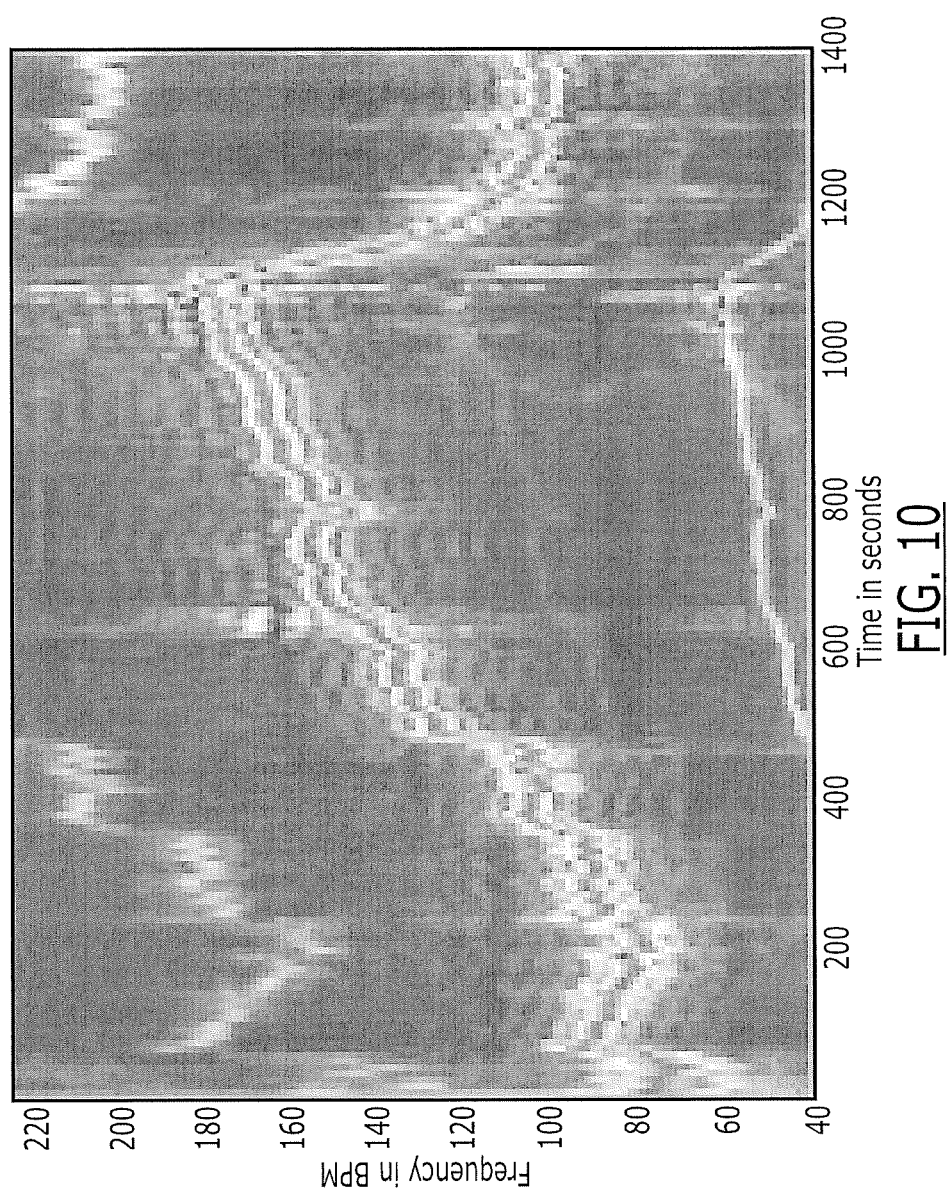
FIGS. 10-15 illustrate measured waveforms according to various embodiments described herein.
Figure 11:
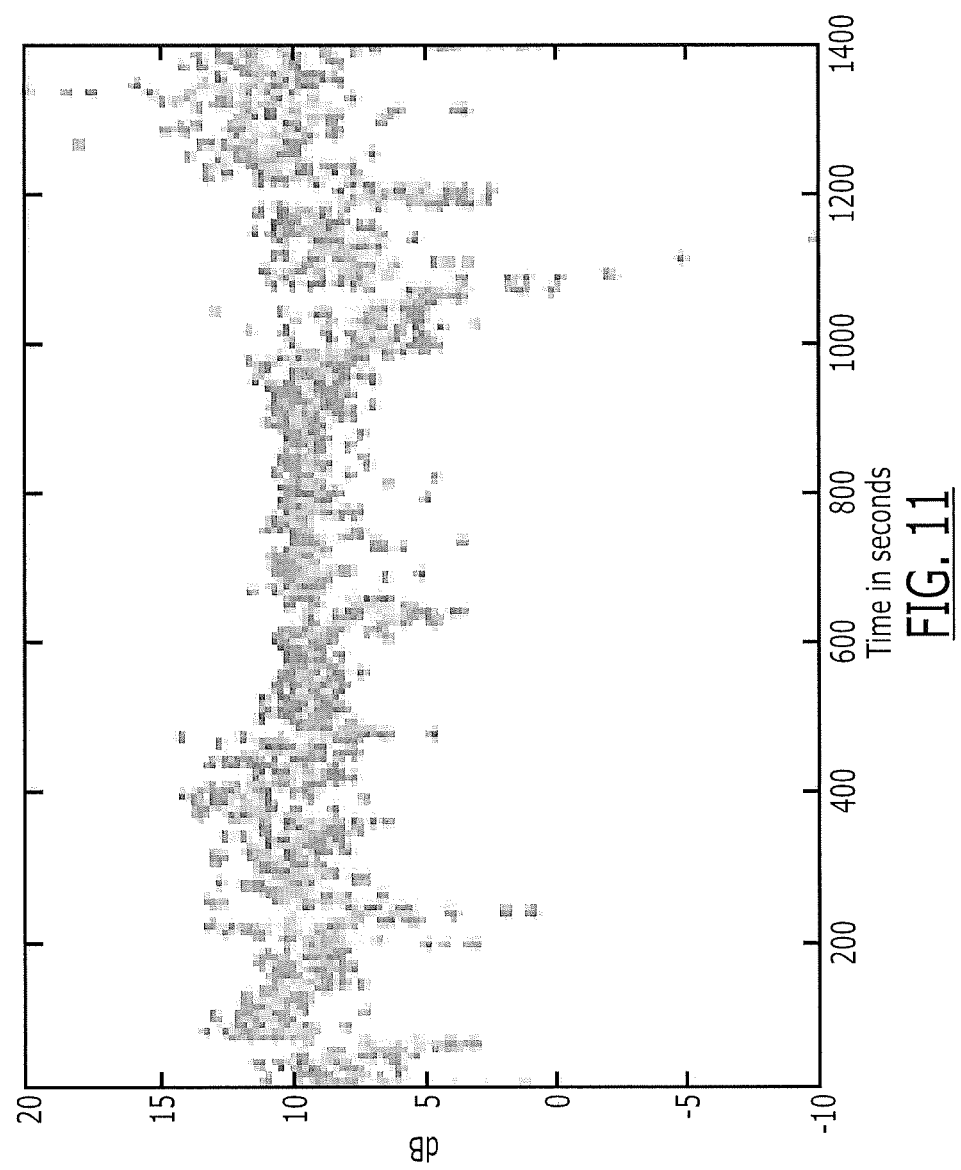

FIG. 11 illustrates a signal-to-noise-and-distortion measurement for the same signal in FIG. 10.

Figure 12:
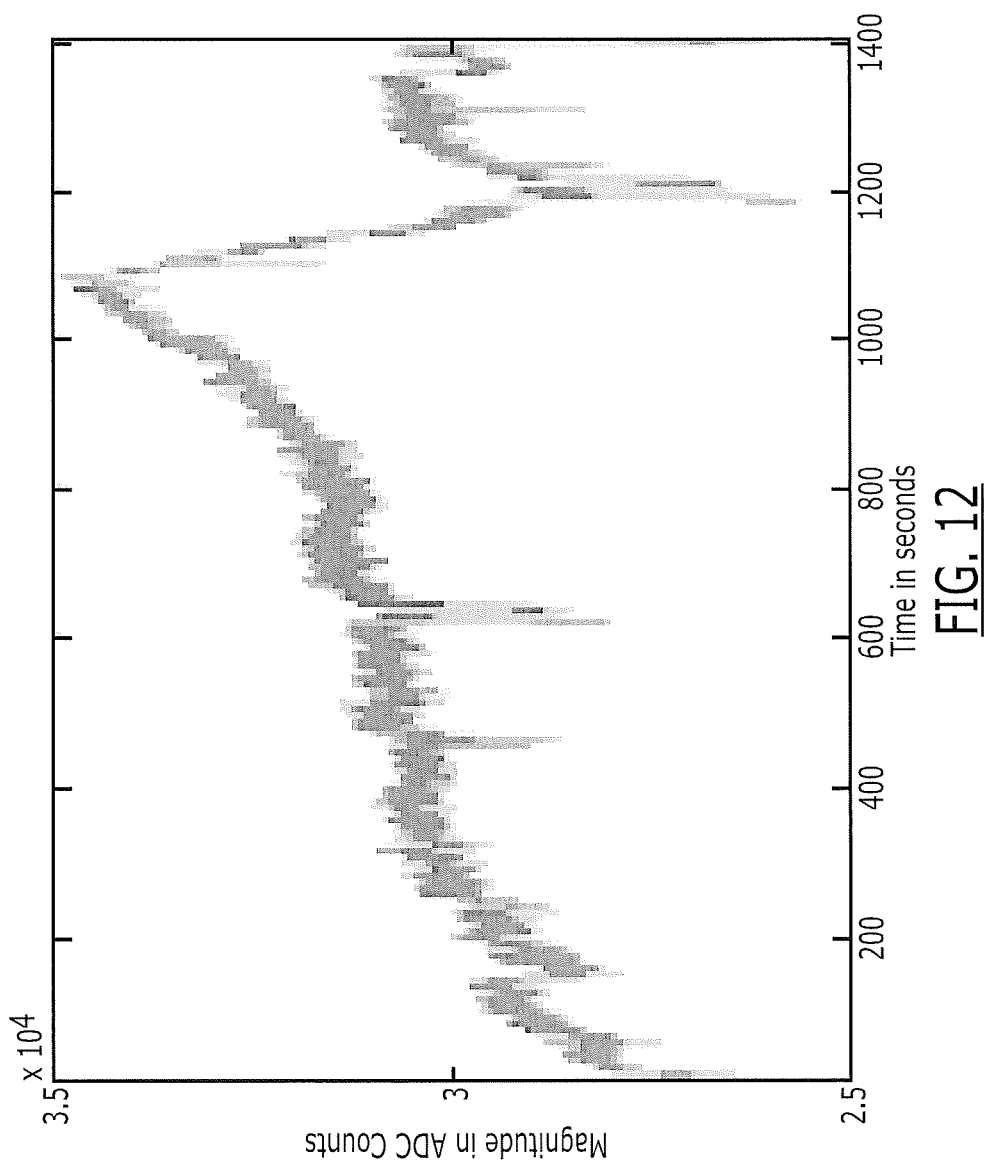

FIG. 12 illustrates raw samples of the physiological waveform 112' that may be obtained by a PPG sensor 110'.

Figure 13:
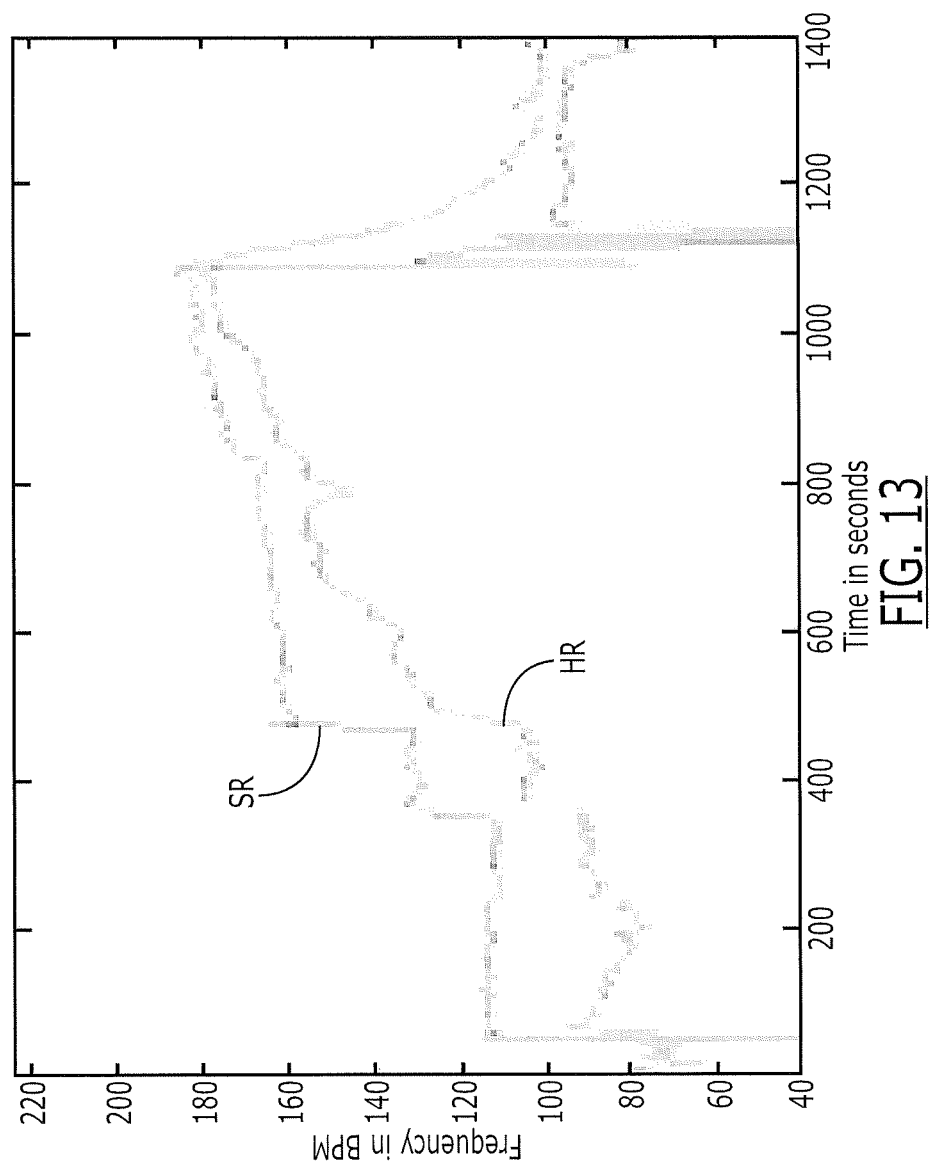

FIG. 13 illustrates heart rate HR (232a of FIG. 4) and step rate SR (in steps per minute) that may be extracted by a system and/or method of FIG. 4 over time.

Figure 14:
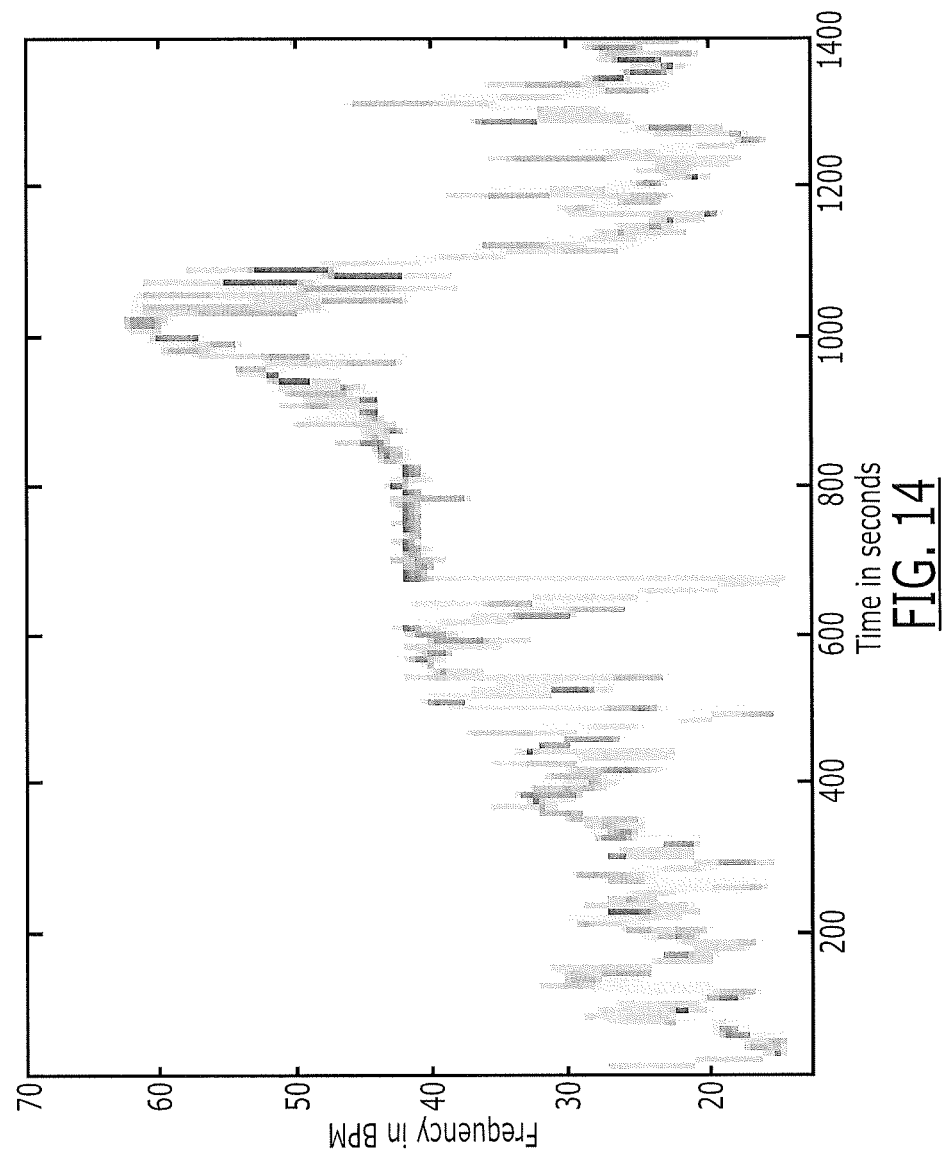
Figure 15:
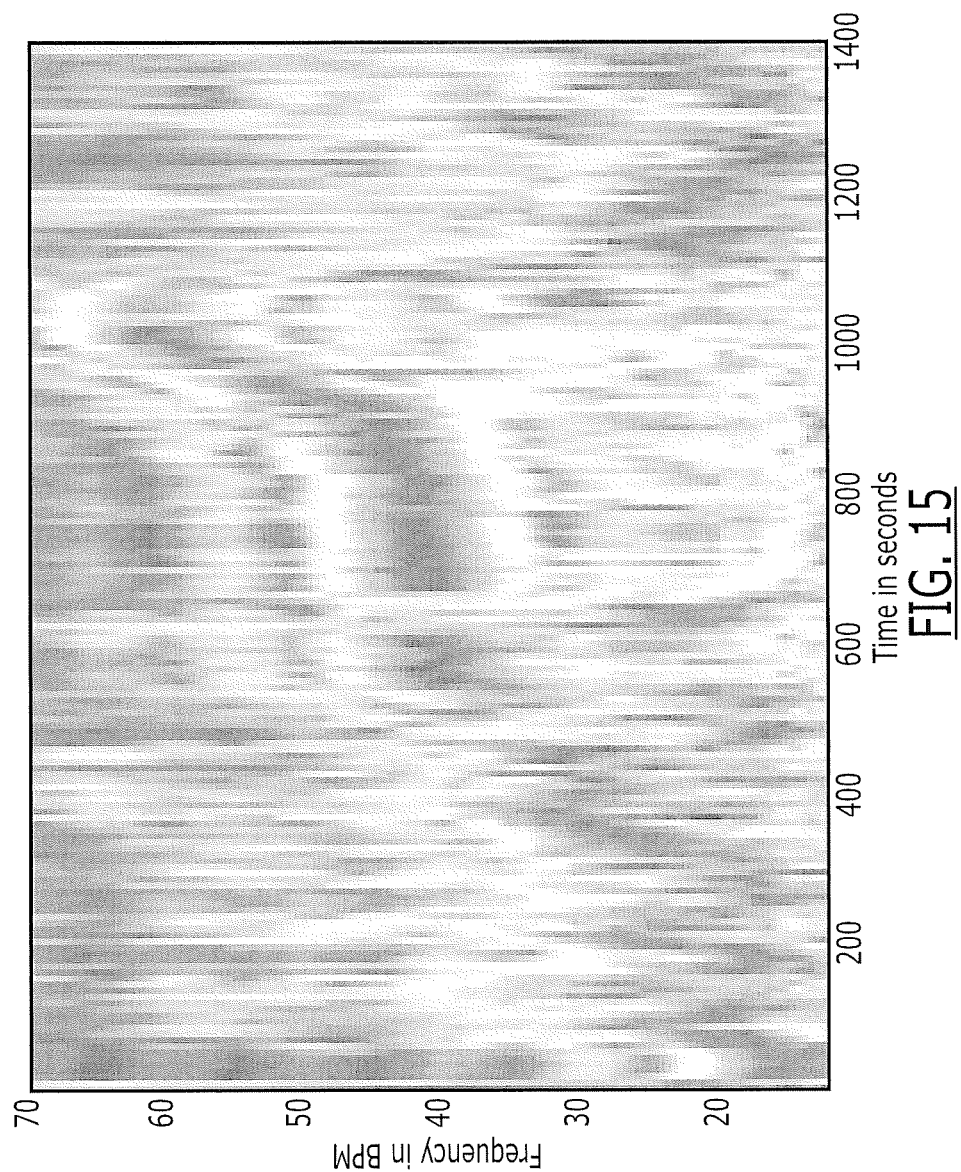

FIG. 14 illustrates a respiration rate metric that may be provided by a respiration rate extractor 230b of FIG. 4 as a function of time. Finally, FIG. 15 illustrates a peak normalized spectrum for the respiration rate.

Various embodiments have been described herein primarily with respect to physiological signal processing systems. However, FIGS. 1-7 also describe analogous physical signal processing methods according to various embodiments described herein. For example, various analogous method embodiments described herein can select among multiple filters for extracting a physiological signal component, where the selection is controlled by an extracted physiological metric. The physiological metric can be the same or different than the physiological component. For example, an extracted heart rate metric can control the filtering of both heart rate and respiration rate. Variable filter adjustment by physiological waveform metric feedback may thereby be provided.

Various embodiments have been described herein with reference to block diagrams and a flowchart of methods, apparatus (systems and/or devices) and/or computer program products. It is understood that a block of the block diagrams and/or flowchart, and combinations of blocks in the block diagrams and/or flowchart, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart, and thereby create means (functionality), structure and/or methods for implementing the functions/acts specified in the block diagrams and/or flowchart.

These computer program instructions may also be stored in a computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-Ray™).

The computer program instructions may also be loaded onto a computer and/or other programmable data processing apparatus to cause a series of operational steps to be performed on the computer and/or other programmable apparatus to produce a computer-implemented process or method such that the instructions which execute on the computer or other programmable apparatus provide steps for implementing the functions/acts specified in the block diagrams and/or flowchart.

Accordingly, the invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the blocks. For example, two blocks shown in succession may in fact be executed substantially concurrently or the blocks may sometimes be executed in the reverse order, depending upon the functionality/acts involved. Moreover, the functionality of a given block of the block diagrams and/or flowchart may be separated into multiple blocks and/or the functionality of two or more blocks of the block diagrams and/or flowchart may be at least partially integrated. Finally, other blocks may be added/inserted between the blocks that are illustrated.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of all combinations and subcombinations of the embodiments described herein, and of the manner and process of making and using them, and shall support claims to any such combination or subcombination.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A physiological signal processing system comprising:
a physiological sensor that is configured to generate a physiological waveform that includes a cardiovascular signal component and a pulmonary signal component comprising overlapping frequency ranges therein;
a variable high pass filter and a variable low pass filter that are coupled to an output of the physiological sensor and are configured to high pass filter and low pass filter the physiological waveform, respectively, in response to at least one corner frequency that is applied thereto;
a respiration rate metric extractor that is coupled to an output of the variable low pass filter and is configured to extract a respiration rate metric from the physiological waveform that is low pass filtered;
a heart rate metric extractor that is coupled to an output of the variable high pass filter and is configured to extract a heart rate metric from the physiological waveform that is high pass filtered; and
a corner frequency adjustor that is coupled to an output of the heart rate metric extractor and is configured to determine the corner frequency that is applied to the variable low pass filter from the heart rate metric that was extracted from the physiological waveform that was high pass filtered.

2. A physiological signal processing system according to claim 1, wherein:
the pulmonary signal component of the physiological waveform is output from the variable low pass filter and the respiration rate metric extractor is configured to extract the respiration rate metric from the pulmonary signal component outputted from the variable low pass filter; and
the cardiovascular signal component of the physiological waveform is output from the variable high pass filter and the heart rate metric extractor is configured to extract the heart rate metric from the cardiovascular signal component outputted from the variable high pass filter.

3. A physiological signal processing system according to claim 1, wherein the physiological waveform comprises a photoplethysmograph (PPG) waveform.

4. A physiological signal processing system according to claim 1, wherein the physiological waveform comprises an electrical physiological waveform including an electroencephalogram (EEG), an electrocardiogram (ECG) and/or a radio frequency (RF) waveform, an electro-optical physiological waveform, an electro-photoacoustic waveform including a photoacoustic waveform, an electro-mechanical physiological waveform including an auscultation waveform, a piezo sensor waveform and/or an accelerometer waveform, and/or an electro-nuclear physiological waveform.

5. A physiological signal processing system according to claim 1, wherein the variable low pass filter comprises a single low pass filter having an adjustable corner frequency.

6. A physiological signal processing system according to claim 1, wherein the variable low pass filter comprises a plurality of low pass filters, a respective one of which includes a different value of the corner frequency, and wherein the corner frequency adjustor is configured to select one of the plurality of low pass filters that corresponds to the corner frequency that is determined.

7. A physiological signal processing system according to claim 1, wherein the variable low pass filter comprises a variable digital low pass filter having a plurality of delay taps and wherein the corner frequency corresponds to a number of the delay taps that are selected to filter the physiological waveform.

8. A physiological signal processing system according to claim 7, wherein the corner frequency adjustor comprises at least one processor configured to map the heart rate metric that is extracted into the number of the delay taps that are selected to low pass filter the physiological waveform.

9. A physiological signal processing system according to claim 1, wherein the corner frequency adjustor is configured to determine the corner frequency that is applied to the variable low pass filter based on the heart rate metric independent of the respiration rate metric.

10. A physiological signal processing system according to claim 8, wherein the corner frequency adjustor is configured to initially set a predetermined corner frequency corresponding to a predetermined heart rate prior to determining the corner frequency that is applied to the variable low pass filter from the heart rate metric.

11. A physiological signal processing system according to claim 1, further comprising:
a physiological metric assessor that is coupled to an output of the respiration rate metric extractor and that is configured to process the respiration rate metric to generate at least one physiological assessment.

12. A physiological signal processing system, comprising:
a variable low pass filter that is responsive to a physiological waveform and that is configured to low pass filter the physiological waveform in response to a corner frequency that is applied thereto;
a respiration rate metric extractor that is coupled to an output of the variable low pass filter and is configured to extract a respiration rate metric from a pulmonary signal component of the physiological waveform that is output from the variable low pass filter responsive to low pass filtering the physiological waveform;
a variable high pass filter that is responsive to the physiological waveform and that is configured to high pass filter the physiological waveform;
a heart rate metric extractor that is coupled to an output of the variable high pass filter and is configured to extract a heart rate metric from a cardiovascular signal component of the physiological waveform that is high pass filtered; and
a corner frequency adjustor coupled to an output of the heart rate metric extractor that is configured to determine the corner frequency that is applied to the variable low pass filter from the heart rate metric extracted by the heart rate metric extractor.

13. A physiological signal processing system according to claim 12,
wherein the variable high pass filter is configured to high pass filter the physiological waveform in response to the corner frequency that is applied thereto.

14. A physiological signal processing system according to claim 12, wherein the physiological waveform comprises a photoplethysmograph (PPG) waveform.

15. A physiological signal processing system according to claim 12, wherein the physiological waveform comprises an electrical physiological waveform including an electroencephalogram (EEG), an electrocardiogram (ECG) and/or a radio frequency (RF) waveform, an electro-optical physiological waveform, an electro-photoacoustic waveform including a photoacoustic waveform, an electro-mechanical physiological waveform including an auscultation waveform, a piezo sensor waveform and/or an accelerometer waveform, and/or an electro-nuclear physiological waveform.

16. A physiological signal processing system according to claim 12, wherein the corner frequency adjustor is configured to determine the corner frequency that is applied to the variable low pass filter based on the heart rate metric independent of the respiration rate metric.

17. A physiological signal processing system according to claim 12, wherein the corner frequency adjustor is configured to determine the corner frequency that is applied to the variable low pass filter from the heart rate metric by applying a margin to the heart rate metric.

18. A physiological signal processing system according to claim 12, further comprising:
a physiological metric assessor that is coupled to an output of the respiration rate metric extractor and that is configured to process the respiration rate metric to generate at least one physiological assessment.

19. A physiological signal processing system according to claim 12, wherein the corner frequency adjustor is configured to initially set a predetermined corner frequency corresponding to a predetermined heart rate prior to determining the corner frequency that is applied to the variable low pass filter from the heart rate metric.

20. A physiological signal processing system according to claim 19, wherein the predetermined heart rate is a resting heart rate.

21. A physiological signal processing system according to claim 19, wherein the corner frequency adjustor is configured to initially set the predetermined corner frequency corresponding to the predetermined heart rate until the heart rate metric extractor locks on a heart rate in the physiological waveform.

22. A physiological signal processing method for a physiological waveform that includes a cardiovascular signal component and a pulmonary signal component therein, the physiological signal processing method comprising:
- executing, by at least one processor, computer program instructions stored in a non-transitory computer readable medium to perform operations comprising:
- low pass filtering the physiological waveform in response to an adjustable low pass filter corner frequency;
- extracting a respiration rate metric from the pulmonary signal component of the physiological waveform that is output from the low pass filtering; and
- determining the adjustable low pass filter corner frequency that is applied to the low pass filtering from a heart rate metric that is extracted from the cardiovascular signal component of the physiological waveform that is high pass filtered by a variable high pass filter.

* * * * *